United States Patent
Keen

(10) Patent No.: US 6,326,215 B1
(45) Date of Patent: Dec. 4, 2001

(54) MOLECULAR WIRE INJECTION SENSORS

(75) Inventor: Randy E. Keen, San Diego, CA (US)

(73) Assignee: KeenSense, Inc., San Diego, CA (US)

( * ) Notice: Subject to any disclaimer, the term of this patent is extended or adjusted under 35 U.S.C. 154(b) by 0 days.

(21) Appl. No.: 09/365,109

(22) Filed: Jul. 30, 1999

Related U.S. Application Data

(62) Division of application No. 08/856,822, filed on May 14, 1997, now Pat. No. 6,060,327.

(51) Int. Cl.$^7$ .................................................. G01N 33/543
(52) U.S. Cl. ....................... 436/518; 204/400; 204/403; 422/82.01; 422/82.02; 427/2.11; 435/6; 435/4; 435/287.1; 435/287.2; 436/149; 436/150; 436/151; 436/524; 436/525; 436/531; 436/806
(58) Field of Search .................................. 204/400, 403; 422/82.01, 82.02; 435/6, 4, 287.1, 287.2; 436/149, 150, 151, 518, 524, 525, 531, 806; 427/2.11

(56) References Cited

U.S. PATENT DOCUMENTS

| | | |
|---|---|---|
| Re. 35,317 | 8/1996 | Lindsay . |
| 4,180,771 | 12/1979 | Guckel .................................. 324/71 |

(List continued on next page.)

FOREIGN PATENT DOCUMENTS

| | | | |
|---|---|---|---|
| 0230472B1 | 6/1986 | (EP) | ............................ G01N/27/416 |
| 0228259B1 | 2/1993 | (EP) | .............................. C12N/11/08 |
| 0395137B1 | 8/1995 | (EP) | ............................ G01N/33/543 |
| WO 93/08464 | 4/1993 | (WO) | ............................. G01N/27/26 |
| WO 94/22889 | 10/1994 | (WO) | . |
| WO 94/28203 | 12/1994 | (WO) | ................................ C25F/3/12 |

OTHER PUBLICATIONS

Arthur J. Frank et al., *Reversible Associative and Dissociative Interactions of Glucose Oxidase with Nitrospiropyran Monolayers Assembled onto Gold Electrodes: Amperometric Transduction of Recorded Optical Signals*, Langmuir; 1996; 12(4); 946–954.

(List continued on next page.)

Primary Examiner—Christopher L. Chin
(74) Attorney, Agent, or Firm—Beyer Weaver & Thomas LLP

(57) ABSTRACT

Disclosed is a sensor for sensing the presence of an analyte component without relying on redox mediators. This sensor includes (a) a plurality of conductive polymer strands each having at least a first end and a second end and each aligned in a substantially common orientation; (b) a plurality of molecular recognition headgroups having an affinity for the analyte component and being attached to the first ends of the conductive polymer strands; and (c) an electrode substrate attached to the conductive polymer strands at the second ends. The electrode substrate is capable of reporting to an electronic circuit reception of mobile charge carriers (electrons or holes) from the conductive polymer strands. The electrode substrate may be a photovoltaic diode. Also disclosed is method of forming a sensor capable of sensing the presence of an analyte component. This method includes (a) contacting a sensor substrate (e.g., a device element of a device on semiconductor chip) with a first medium containing mobile conductive polymer strands or precursors of the conductive polymer strands; (b) applying a first potential to the substrate sufficient to form a first structure having the conductive polymer strands affixed into the substrate; (c) contacting the sensor substrate, with affixed conductive polymer strands, with a second medium containing mobile molecular recognition headgroups; and (d) applying a second potential to the substrate sufficient to affix the molecular recognition headgroups to the affixed conductive polymer strands.

27 Claims, 6 Drawing Sheets

U.S. PATENT DOCUMENTS

| | | | |
|---|---|---|---|
| 4,218,298 | 8/1980 | Shimada et al. | 204/195 |
| 4,225,410 | 9/1980 | Pace | 204/195 |
| 4,354,308 | 10/1982 | Shimada et al. | 29/571 |
| 4,416,959 | 11/1983 | Skotheim | 429/111 |
| 4,442,185 | 4/1984 | Skotheim | 429/111 |
| 4,502,938 | 3/1985 | Covington et al. | 204/412 |
| 4,545,382 | 10/1985 | Higgins et al. | 128/635 |
| 4,562,157 | 12/1985 | Lowe et al. | 435/291 |
| 4,591,550 | 5/1986 | Hafeman et al. | 435/4 |
| 4,655,885 | 4/1987 | Hill et al. . | |
| 4,711,245 | 12/1987 | Higgins et al. | 128/635 |
| 4,713,347 | 12/1987 | Mitchell et al. | 436/501 |
| 4,717,673 | 1/1988 | Wrighton et al. | 436/68 |
| 4,721,601 | 1/1988 | Wrighton et al. | 422/68 |
| 4,764,797 | 8/1988 | Shaw et al. | 357/25 |
| 4,777,019 | 10/1988 | Dandekar | 422/68 |
| 4,839,000 | 6/1989 | Eddowes | 204/1 |
| 4,874,500 | 10/1989 | Madou et al. | 204/412 |
| 4,886,625 | 12/1989 | Albarella et al. | 252/500 |
| 4,889,612 | 12/1989 | Geist et al. | 204/416 |
| 4,894,339 | 1/1990 | Hanazato et al. | 435/182 |
| 4,895,705 | 1/1990 | Wrighton | 422/68 |
| 4,909,921 | 3/1990 | Ito | 204/403 |
| 4,916,075 | 4/1990 | Malmros et al. | 435/291 |
| 4,929,313 | 5/1990 | Wrighton | 204/153.1 |
| 4,936,956 | 6/1990 | Wrighton | 204/153.21 |
| 4,942,127 | 7/1990 | Wada et al. | 435/11 |
| 4,963,815 | 10/1990 | Hafeman | 324/715 |
| 5,000,180 | 3/1991 | Kuypers et al. | 128/635 |
| 5,034,192 | 7/1991 | Wrighton et al. | 422/82.02 |
| 5,063,081 | 11/1991 | Cozzette et al. | 427/2 |
| 5,089,112 | 2/1992 | Skotheim et al. . | |
| 5,108,819 | 4/1992 | Heller et al. | 428/195 |
| 5,112,455 | 5/1992 | Cozzette et al. | 204/153.12 |
| 5,126,921 | 6/1992 | Fujishima et al. | 361/525 |
| 5,140,393 | 8/1992 | Hijikihigawa et al. | 357/25 |
| 5,156,810 | 10/1992 | Ribi | 422/82.01 |
| 5,166,063 | 11/1992 | Johnson | 435/173 |
| 5,200,051 | 4/1993 | Cozzette et al. | 204/403 |
| 5,202,261 | 4/1993 | Musho et al. | 435/288 |
| 5,212,050 | 5/1993 | Mier et al. | 430/320 |
| 5,215,631 | 6/1993 | Westfall | 204/64 |
| 5,243,516 | 9/1993 | White | 364/413.07 |
| 5,250,168 | 10/1993 | Tsukada et al. | 204/416 |
| 5,252,743 | 10/1993 | Barrett et al. | 548/303.7 |
| 5,262,035 | 11/1993 | Gregg et al. | 204/403 |
| 5,264,092 | 11/1993 | Skotheim et al. . | |
| 5,264,104 | 11/1993 | Gregg et al. . | |
| 5,264,105 | 11/1993 | Gregg et al. . | |
| 5,309,085 | 5/1994 | Sohn | 324/71.5 |
| 5,320,725 | 6/1994 | Gregg et al. | 204/153.12 |
| 5,320,736 | 6/1994 | Stickney et al. | 205/157 |
| 5,356,757 | 10/1994 | Shionoya et al. | 430/315 |
| 5,385,651 | 1/1995 | Stickney et al. | 204/109.25 |
| 5,401,376 | 3/1995 | Foos et al. | 204/415 |
| 5,403,451 | 4/1995 | Riviello et al. | 204/153.1 |
| 5,403,700 | 4/1995 | Heller et al. | 430/311 |
| 5,411,647 | 5/1995 | Johnson et al. . | |
| 5,422,246 | 6/1995 | Koopal et al. | 435/14 |
| 5,431,883 | 7/1995 | Barraud | 422/82.01 |
| 5,466,589 | 11/1995 | Olinger et al. . | |
| 5,491,097 | 2/1996 | Ribi et al. | 436/518 |
| 5,532,128 | 7/1996 | Eggers et al. | 435/16 |
| 5,534,132 | 7/1996 | Vreeke et al. | 205/777.5 |
| 5,543,326 | 8/1996 | Heller et al. | 435/287.9 |
| 5,556,524 | 9/1996 | Albers | 204/296 |
| 5,556,752 | 9/1996 | Lockhart et al. | 435/6 |
| 5,561,071 | 10/1996 | Hollenberg et al. | 437/1 |
| 5,571,568 | 11/1996 | Ribi et al. | 427/487 |
| 5,591,578 | 1/1997 | Meade et al. | 435/6 |
| 5,593,852 | 1/1997 | Heller | 435/14 |
| 5,622,872 | 4/1997 | Ribi | 436/518 |
| 5,665,222 | 9/1997 | Heller et al. . | |
| 5,670,322 | 9/1997 | Eggers et al. | 435/6 |
| 5,705,348 | 1/1998 | Meade et al. . | |
| 5,770,369 | 6/1998 | Meade et al. . | |
| 5,780,234 | 7/1998 | Meade et al. . | |
| 5,824,473 | 10/1998 | Meade et al. . | |
| 5,837,859 | 11/1998 | Teoule et al. . | |
| 5,874,046 | 2/1999 | Megerle . | |
| 5,922,183 | 7/1999 | Rauh . | |
| 5,952,172 | 9/1999 | Meade et al. . | |
| 5,972,199 | 10/1999 | Heller et al. . | |
| 6,013,170 | 1/2000 | Meade . | |
| 6,013,459 | 1/2000 | Meade . | |
| 6,060,023 | 5/2000 | Maracas . | |
| 6,071,699 | 6/2000 | Meade et al. . | |
| 6,087,100 | 7/2000 | Meade et al. . | |
| 6,090,933 | 7/2000 | Kayyem et al. . | |
| 6,096,273 | 8/2000 | Kayyem et al. . | |
| 6,117,973 | 9/2000 | Batz et al. . | |
| 6,134,461 | 11/2000 | Say et al. . | |
| 6,177,250 | 1/2001 | Meade et al. . | |
| 6,180,352 | 1/2001 | Meade et al. . | |
| 6,197,949 | 3/2001 | Teoule et al. . | |
| 6,200,761 | 3/2001 | Meade et al. . | |

OTHER PUBLICATIONS

Ravi Rajagopalan et al., *Effect of Quaternization of the Glucose Oxidase "Wiring" Redox Polymer on the Maximum Current Densities of Glucose Electrodes*, The Journal of Physical Chemistry; 100(9); 3719–3727.

Ron Blonder et al., *Application of a Nitrospiropyran–FA-D–Reconstituted Glucose Oxidase and Charged Electron Mediators as Optobioelectronic Assemblies for the Amperometric Transduction of Recorded Optical Signals: Control of the "On"–"Off" Direction of the Photoswitch*, Journal of the American Chemical Society; 1997; 119(49); 11747–11757.

Pedro Alzari et al., *Molecular Recognition of Artificial Single–Electron Acceptor Cosubstrates by Glucose Oxidase?*, Journal of the American Chemical Society; 1996; 118(28); 6788–6789.

Zhanen Zhang et al., *A Glucose Biosensor Based on Immobilization of Glucose Oxidase in Electropolymerized o–Aminophenol Film on Platinized Glassy Carbon Electrode*, Analytical Chemistry; 1996; 68(9); 1632–1638.

Guoqiong Du et al., *Electroanalytical Detection of Glucose Using a Cyanometalate–Modified Electrode: Requirements for the Oxidation of Buried Redox Sites in Glucose Oxidase*, Analytical Chemistry; 1996; 68(5); 796–806.

Amos Bardea, et al., *NAD+–Dependent Enzyme Electrodes: Electrical Contact of Cofactor–Dependent Enzymes and Electrodes*, Journal of the American Chemical Society; 1997; 119(39); 9114–9119.

Wolfgang Wernet, *Design of Enzyme Electrodes for Extended Use and Storage Life*, Analytical Chemistry; 1997; 69(14); 2682–2687.

C. Danilowicz and L. Diaz, *Electrical Communication between Electrodes and Enzymes Mediated by Redox Hydrogels*, Analytical Chemistry; 1996; 68(23); 4186–4193.

Yoshio Okahata, et al., *Orientation of DNA Double Strands in a Langmuir–Blodgett Film*, Langmuir; 1996; 12(5); 1326–1330.

Alaa–Eldin F. Nassar et al., *Electron Transfer between Electrodes and Heme Proteins in Protein–DNA Films*, Journal of the American Chemical Society; 1996; 118(12); 3043–3044.

Joseph Wang et al., *Peptide Nucleic Acid Probes for Sequence–Specific DNA Biosensors*, Journal of the American Chemical Society; 1996; 118(33); 7667–7670.

P. N. Bartlett et al., *Modification of Glucose Oxidase by the Covalent Attachment of a Tetrathiafulvalene Derivative*, Analytical Chemistry; 1997; 69(4); 734–742.

Sayed A. M. Marzouk et al., *A Conducting Salt–Based Amperometric Biosensor for Measurement of Extracellular Lactate Accumulation in Ischemic Myocardium*, Analytical Chemistry; 1997; 69(14); 2646–2652.

Serge Cosnier, et al., *An Electrochemical Method for Making Enzyme Microsensors. Application to the Detection of Dopamine and Glutamate*, Analytical Chemistry; 1997; 69(5); 968–971.

Won Jun Sung and You Han Bae, *A Glucose Oxidase Electrode Based on Electropolymerized Conducting Polymer with Polyanion–Enzyme Conjugated Dopant*, Analytical Chemistry; 2000; 72(9); 2177–2181.

T. de Lumley–Woodyear, C. N. Campbell, and A. Heller, *Direct Enzyme–Amplified Electrical Recognition of a 30–Base Model Oligonucleotide*, Journal of the American Chemical Society; 1996; 118(23); 5504–5505.

Itamar Willner et al., *Electrical Wiring of Glucose Oxidase by Reconstitution of FAD–Modified Monolayers Assembled onto Au–Electrodes*, Journal of the American Chemical Society; 1996; 118(42); 10321–10322.

Gregg Kenausis et al., *Electrochemical Glucose and Lactate Sensors Based on "Wired" Thermostable Soybean Peroxidase Operating Continuously and Stably at 37° C.*, Analytical Chemistry; 1997; 69(6); 1054–1060.

Yuri M. Lvov, et al., *Direct Electrochemistry of Myoglobin and Cytochrome P450cam in Alternate Layer–by–Layer Films with DNA and Other Polyions*, Journal of the American Chemical Society; 1998; 120(17); 4073–4080.

James F. Rusling, *Enzyme Bioelectrochemistry in Cast Biomembrane–Like Films*, Accounts of Chemical Research; 1998; 31(6); 363–369.

Achim Stocker and Andreas F. Bückmann, *Reconstitution of Apo–Glucose Oxidase with a Nitrospiropyran–Modified FAD Cofactor Yields a Photoswitchable Biocatalyst for Amperometric Transduction of Recorded Optical Signals*, Journal of the American Chemical Society; 1996; 118(22); 5310–5311.

Itamar Willner, *Photoswitchable Biomaterials: En Route to Optobioelectronic Systems*, Accounts of Chemical Research; 1997; 30(9); 347–356.

Golam Faruque Khan et al., *Design of a Stable Charge Transfer Complex Electrode for a Third–Generation Amperometric Glucose Sensor*, Analytical Chemistry; 1996; 68(17); 2939–2945.

Philip N. Bartlett, *Layer–by–Layer Self–Assembly of Glucose Oxidase with a Poly(allylamine)ferrocene Redox Mediator*, Langmuir; 1997; 13(10); 2708–2716.

Joseph Wang and Prasad V. A. Pamidi, *Sol–Gel–Derived Gold Composite Electrodes*, Analytical Chemistry; 1997; 69(21); 4490–4494.

Y. Okahata, et al., *DNA–Aligned Cast Film and its Anisotropic Electron Conductivity*, Supramolecular Science; 1998; 5(3–4); 317–320.

Yoshio Okahata et al., *Oriented Thin Films of a DNA–Lipid Complex*, Thin Solid Films; 1996; 284–285; 6–8.

Masatsugu Shimomura et al., *Construction of Oriented p–Electron Arrays Based on Two–Dimensional Supramolecular Organizates*, Supramolecular Science; 1996; 3(1–3); 61–65.

T. Livache, et al., *Biosensing Effects in Functionalized Electroconducting Conjugated Polymer Layers: Addressable DNA Matrix for the Detection of Gene Mutations*, Synthetic Metals; 1995; 71(1–3); 2143–2146.

A. Guerrieri et al., *Electrosynthesized Non–Conducting Polymers as Permselective Membranes in Amperometric Enzyme Electrodes: A Glucose Biosensor Based On a Co–Crosslinked Glucose Oxidase/Overoxidized Polypyrrole Bilayer*, Biosensors & Bioelectronics; 1998; 13(1); 103–112.

M. Trojanowicz, et al., *Biosensors Based on Oxidase Immobilized in Various Conducting Polymers*, Sensors and Actuators B: Chemical; 1995; 28(3); 191–199.

Tetsuya Haruyama et al., *Electron Transfer Between an Electrochemically Deposited Glucose Oxidase/Cu[II] Complex and an Electrode*, Biosensors & Bioelectronics; 1998; 13(9); 1015–1022.

Itamar Willner et al., *Photoswitchable Biomaterials as Grounds for Optobioelectronic Devices*, Biochemistry and Bioenergetics; 1997; 42(1); 43–57.

P. J. H. J. van Os et al., *Glucose Detection at Bare and Sputtered Platinum Electrodes Coated With Polypyrrole and Glucose Oxidase*, Analytica Chimica Acta; 1996; 335(3); 209–216.

Shaik M. Zakeeruddin et al., *Glucose Oxidase Mediation by Soluble and Immobilized Electroactive Detergents*, Biosensors & Bioelectronics; 1996; 11(3); 305–315.

Sergey D. Varfolomeev et al., *Direct Electron Transfer Effect Biosensors*, Biosensors & Bioelectronics; 1996; 11(9); 863–871.

M. Alvarez–Icaza et al., *The Design of Enzyme Sensors Based on the Enzyme Structure*, Biosensors & Bioelectronics; 1995; 10(8); 735–742.

C. Danilowicz et al., *An Os(byp)2ClPyCH2NH Poly(allylamine) Hydrogel Mediator for Enzyme Wiring at Electrodes*, Electrochimica Acta; 1998; 43(23); 3525–3531.

Willem M. Albers et al., *Design of Novel Molecular Wires for Realizing Long–Distance Electron Transfer*, Bioelectrochemistry and Bioenergetics; 1997; 42(1); 25–33.

Eugenii Katz, et al., *Electrical Contact of Redox Enzymes with Electrodes: Novel Approaches for Amperometric Biosensors*, Bioelectrochemistry and Bioenergetics; 1997; 42(1); 95–104.

Wolfgang Schuhmann, *Electron–Transfer Pathways in Amperometric Biosensors. Ferrocene–Modified Enzymes Entrapped in Conducting–Polymer Layers*, Biosensors & Bioelectronics; 1995; 10(1–2); 181–193.

K. Warriner et al., *Stability of Dodecyl Sulphate–Doped Poly(pyrrole)/Glucose Oxidase Modified Electrodes Exposed in Human Blood Serum*, Materials Science and Engineering: C; 1997; 5(2); 81–90.

J. Li et al., *Mediated Amperometric Glucose Sensor Modified by the Sol–Gel Method*, Sensors and Actuators B: Chemical; 1997; 40(2–3); 135–141.

Golam Faruque Khan, *Construction of SEC/CTC Electrodes for Direct Electron Transferring Biosensors*, Sensors and Actuators B: Chemical; 1996; 36(1–3); 484–490.

Shaolin Mu et al., *Bioelectrochemical Characteristics of Glucose Oxidase Immobilized in a Polyaniline Film*, Sensors and Actuators B: Chemical; 1996; 31(3); 155–160.

Joong–Hoon Cho et al., *Electrochemical Adsorption of Glucose Oxidase Onto Polypyrrole Film for the Construction of a Glucose Biosensor*, Sensors and Actuators B: Chemical; 1996; 30(2); 137–141.

Min–Choi Shin et al., *Electrochemical Characterization of Polypyrrole/Glucose Oxidase Biosensor: Part I. Influence of Enzyme Concentration on the Growth and Properties of the Film*, Biosensors & Bioelectronics; 1996; 11(1–2); 161–169.

Min–Choi Shi, et al., *Electrochemical Characterization of Polypyrrole/Glucose Oxidase Biosensor: Part II. Optimal Preparation Conditions for the Biosensor*, Biosensors & Bioelectronics; 1996; 11(1–2); 171–178.

K. Warriner et al., *Electrochemical Characteristics of Two Model Electropolymerised Films for Enzyme Electrodes*, Biosensors & Bioelectronics; 1996; 11(6–7); 615–623.

G.E. De Benedetto et al., *One–Step Fabrication of a Bienzyme Glucose Sensor Based on Glucose Oxidase and Peroxidase Immobilized Onto a Poly(pyrrole) Modified Glassy Carbon Electrode*, Biosensors & Bioelectronics; 1996; 11(10); 1001–1008.

Kumaran Ramanathan et al., *Application of Polyaniline–Langmuir–Blodgett Films as a Glucose Biosensor*, Materials Science and Engineering: C; 1995; 3(3–4); 159–163.

L. Coche–Gurente, et al., *Development of Amperometric Biosensors Based on the Immobilization of Enzymes in Polymer Films Electrogenerated From a Series of Amphiphilic Pyrrole Derivatives*, Analytica Chimica Acta; 1995; 311(1); 23–30.

Qijin Chi, et al., *Amperometric Biosensors Based on the Immobilization of Oxidases in a Prussian Blue Film by Electrochemical Codepostiton*, Analytica Chimica Acta; 1995; 310(3); 429–436.

Jingdong Zhang et al., *A Comparative Study on STM Imaging and Electrocatalytic Activity of Different Sufraces Modified with Flavin Adenine Dinucleotide*, Electrochimica Acta; 1995; 40(6); 733–744.

Miloslav Pravda et al., *Evaluation of Amperometric Glucose Biosensors Based on Co–Immobilisation of Glucose Oxidase with an Osmium Redox Polymer in Electrochemically Generated Polyphenol Films*, Analytica Chimica Acta; 1995; 304(2); 127–138.

Carl A. Koval et al., *Electron Transfer at Semiconductor Electrode–Liquid Electrolyte Interfaces*, Chemical Reviews; 1992; 92(3); 411–433. (Review).

Heller, A: "Electrical Wiring of Redox Enzymes." *Acc. Chem. Res.* 23(5):128–134, 1990.

Khan, GF; Shinohara, H; Ikariyama, y; Aizawa, M: "Electrochemical Behaviour of Monolayer Quinoprotein Adsorbed on the Electrode Surface," *J. Electroanal Chem.* 315:263–273, 1991.

Shinohara, H; Khan, GF; Ikariyama, Y; Aizawa, M: "Electrochemical Oxidation and Reduction of PQQ Using a Conducting Polypyrrole–Coated Electrode," *J. Electroanal, Chem.* 304:75–84, 1991.

Schuhmann, W; Ohara, TJ; Schmidt, H–L; Heller, A: "Electron Transfer between Glucose Oxidase and Electrodes via Redox Mediators Bound with Flexible Chains to the Enzyme Surface," *J. Am. Chem. Soc.* 113(4):1394–1397, 1991.

Gregg, BA; Heller, A: "Cross–Linked Redox Gels Containing Glucose Oxidase for Amperometric Biosensor Applications," *Anal Chem.* 62(3):258–263, 1990.

Heller, A: "Electrical Connection of Enzyme Redox Centers to Electrodes," *J. Phys. Chem.* 96(9):3579–3587, 1992.

Schuhmann, W: "Diagnostic Biosensor Polymers," ACS Symposium Series 556. Usmani, AM; Akmal, N; eds. *American Chemical Society*; Washington, D.C.; 1994; pp. 110–123.

Heller, A: "Electrical Wiring of Redox Enzymes," *Acc. Chem. Res.* 23(5):128–134, 1990.

Wrotnowski, Cort, "Biosensors are Making Steady Yet Limited Progress into the Marketplace," 11–15–96, *Genetic Engineering News*.

Dagani, Ron, "Single molecular wire shown to be conductive," 3–15–96, *C&EN*.

Gregg, BA: Heller, "A:Redox Polymer Films Containing Enzymes.1. A Redox–Conducting Epoxy Cement: Synthesis, Characterization, and Electrocatalytic Oxidation of Hydroquinone." *J Phys. Chem.* 95:5970–5975, 1991.

Hale, PD et al. "A New Class of Amperometric Biosensor Incorporating a Polymeric Electron–Transfer Mediator." *J. Am. Chem. Soc.* 111(9): 3482–3484, 1989.

Cass, AEG, et al. "Ferrocene–Mediated Enzyme Electrode for Amperometric Determination of Glucose," *Anal. Chem.* 56:667–671, 1984.

Kober, EM, et al. "Synthetic Routes to New Polpyridyl Complexes of Osmium (II)," *Inorg. Chem.* 27: 4587–4598, 1988.

Boguslavsky, LI et al. "Novel Biosensors for Specific Neurotransmitters Based on Flavoenzymes and Flexible Redox Polymers," *Polym. Mater. Sci. Eng.* 64:322–323, 1991.

Marcus, RA, et al. "Electron Transfers In Chemistry and Biology Biochim," *Biophys. Acta* 811:265–322, 1985.

Abstract. KAMR Proprietary. "Superconducting Quantum Wire Injection Device—A Novel Molecular Transistor," *US Patent Application*. KAMR Proprietary. 1–37. Dec. 01, 1991.

Aizawa, M. et al., "Molecular Interfacing of Enzymes on the Electrode Surface," Chapter 26. In: Interfacial Design and Chemical Sensing. ACS Symposium Series 561. Mallouk, TE; Harrison, DJ ; eds. *American Chemical Society*, Washington, D. C.: 305–314, 1994.

Boehringer, et al., "Electron–Transport Rates in an Enzyme Electrode for Glucose," ACS Symposium Series, *American Chemical Society*, Washington, D.C., 1994, pp. 47–306.

Collings, PJ: Chap. 9. "Polymer Liquid Crystals," In: Liquid Crystals: Nature's Delicate Phase of Matter. *Princeton University Press*; Princeton, New Jersey, 162–180; 1990.

Ladik, J; Biczo, G; Redly, J: "Possibility of Superconductive–Type Enhanced Conductivity in DNA at Room Temperature." *Phys. Rev.* 188(2):710–715, 1969.

Ahmed, NAG; Calderwood, JH; Frohlich, H; Smith, CW: "Evidence For Collective Magnetic Effects In An Enzyme: Likelihood Of Room Temperature Superconductive Regions," *Phys. Lett.* 53A(2):129–130, 1975.

Little, WA: "Possibility of Synthesizing an Organic Superconductor," *Phys. Rev.* 134(6A):A1416–A1424, 1964.

Little, WA: "Possibility of Synthesizing an Organic Superconductor," *Phys. Rev.* 134(6A):A1416–A1424, 1964.

Kulys, JJ, et al.: "Oxidation Of Glucose Oxidase From Penicillin Vitale By One– And Two–Electron Acceptors," *Biochim. Biophys. Acta* 744:57–63, 1983.

Ikeda, T; et al. M: "Glucose Oxidase–Immobilized Benzoquinone–Carbon Paste Electrode as a Glucose Sensor," *Agric. Biol. Chem.* 49(2):541–543, 1985.

Matthews, FS;, et al.: "The Structure of Cytochrome $b_{562}$ from *Escherichia coli* at 2.5 Å Resolution," *J. Biol. Chem.* 254(5):1699–1706, 1979.

Weber, PC; et al.: "On the Evolutionary Relationship of the 4–_–Helical Heme Proteins," *J. Biol. Chem.* 256(15):7702–7704, 1981.

Lambrechts, M; Sansen, W: Chap. 4. "Planar Technologies For Microelectrochemical Sensors. In: Biosensors: Microelectrochemical Devices," *Institute of Physics Publishing*, Bristol, Philadelphia, New York; 1992; pp. 98–155.

Launay, JP: "Intermolecular Electron Transfer. Applications In Molecular Electronics. In: Mixed Valency Systems: Applications In Chemistry, Physics and Biology," Prassides, K; ed. *Kluwer Academic Publishers*; Dordrecht, Boston, London; 1991; pp. 321–328.

Pethig, R: "Electronic Properties of Biological Materials," *John Wiley & Sons*, Chichester and New York, 1979.

Carter, F., "Molecular Electronic Devices II," *Marcel Dekker, Inc.*, New York and Basel; 1987, pp. 39–53; 269–310, 573–590 and 723–739.

Stegemeyer, H; "Liquid Crystals," Steinkopff, Darmstadt and Springer, New York; 1994; Chapters 1–3.

Degani, Y; Heller A: "Direct Electrical Communication between Chemically Modified Enzymes and Metal Electrodes," 1. *Electron Transfer from Glucose* 20(1):78–81, 1979.

Miller, LL: Mann, KR: "π– Dimers and π–Stacks in Solution and in Conducting Polymers," *Acc. Chem. Res.* 29(9):417–423.

Herzfeld, J: "Entropically Driven Order in Crowded Solutions: From Liquid Crystals to Cell Biology," *Acc. Chem. Res.*, 1996, pp. 31–37.

Stix, G: "Trends in Semiconductor Manufacturing: Toward Point One," *Scientific American* 272(2):90–95, 1995.

Arkin, MR; et al.: "Rates of DNA–Mediated Electron Transfer Between Metallointercalators," *Science* 273:475–480, 1996.

Meade, TJ and Kayyem, JF: "Electron Transfer Through DNA: Site–Specific Modification of Duplex DNA with Ruthenium Donors and Acceptors," *Angew. Chem. Int. Ed. Engl.*34(3):352–354, 1995.

Sailor, MJ; Curtis, CL: "Conducting Polymer Connections for Molecular Devices," *Adv. Mater.* 6(9):688–692, 1994.

Kressin, AM; et al.: "Synthesis of Stoichiometric Cadmium Selenide Films via Sequential Monolayer Electrodeposition," *Chem. Mater.* 3(6):1015–1020, 1991.

Booy, FP; et al.: "Liquid–Crystalline, Phase–Like Packing Of Encapsulated DNA In Herpes Simplex Virus," *Cell* 64:1007–1015, 1991.

Flory, PJ: "Nematic Phase Equilibrium in Rigid Chain Polymers," *Polymer Preprints* 20(1):30, 1979.

Iizuka, E: "Liquid Crystals of Macromolecules Including Living Systems: With Stress on Their Susceptibilities to Electromagnetic Fields," *Polymer Preprints* 20(1):78–81, 1979.

Rill, RL: "Liquid Crystalline Phases in Concentrated Aqueous Solutions of Na$^{+DNA}$," *Proc. Natl. Acad. Sci. USA* 83:342–346, 1986.

Brandes, R; Kearns, DR: "Magnetic Ordering of DNA Liauid Crystals," *Biochemistry* 25(20):5890–5895, 1986.

Alam, TM; Orban, J; Drobny, G: "A Solid–State Deuterium NMR Investigation of Conformation and Order in Magnetically Oriented [d(CGCGAATTCGCG)]$_2$" *Biochemistry* 29(41):9610–9617, 1990.

Wang, J; Angnes, L: Miniaturized "Glucose Sensors Based on Electrochemical Codeposition Of Rhodium And Glucose Oxidase Onto Carbon–Fiber Electrodes," *Anal. Chem.* 64:456–459, 1992.

Lee, YC; Mendoza, BS: "Possible High–$T_c$ Superconductivity in Thin Wires." *Phys. Rev.* B39(7):4776–4779, 1989.

Canright, GS; Vignale, G: "Superconductivity and Acoustic Plasmons in the Two–Dimensional Electron Gas," *Phys. Rev.* B39(4):2740–2743, 1989.

Felts, AK; et al.: "Multilevel Redfield Treatment of Bridge–Mediated Long– Range Electron Transfer: A Mechanism for Anomalous Distance Dependence," *J. Phys. Chem*: 99:2929–2940, 1995.

Van Zandt, LL; Sazena, VK: "DNA Plasmons," *Phys. Rev. Lett* 61(15):1788–1790, 1988.

Sokoloff, JB: "Comment on DNA Plasmon," *Phys. Rev. Lett.* 63(20):2316, 1989.

Povsic, TJ; et al.: "Triple Helix Formation By Oligonucleotides On DNA Extended To The Physiological pH Range," *J. Am. Chem. Soc.* 111(8):3059–3061, 1989.

Maeda, M; et al.: "Mg$^{2+}$–Selective Electrode Comprising Double–Helical DNA as Receptive Entity," *Chem. Lett.* 1994:1805–1808, 1994.

Lvov, Y; Decher, G; Sukhorukov, G: "Assembly of Thin Films by Means of Successive Deposition of Alternate Layers of DNA and Poly(Allylamine)," *Macromolecules* 26:5396–5399, 1993.

Ijiro, K and Okahata, Y: "A DNA–Lipid Complex Soluble in Organic Solvents," *J. Chem. Soc., Chem. Commun.* 1992:1339, 1992.

Tanatar, B: "Collective Modes in a Quasi–One Dimensional, Two–Component Electron Liquid," *Solid State Communications* 92(8):699–702, 1994.

Ruvalds, J: "Plasmons and High–Temperature Superconductivity in Alloys of Copper Oxides," *Phys. Rev.* B35(16):8869–8872, 1987.

Bakhshi, AK: "Investigation of Electronic Conduction in Proteins and DNA" *Prog. Biophys. Molec. Biol.* 61:187–253, 1994.

Bardeen, J; Brattain, WH: "The Transistor, A Semi–Conductor Triode." *Phys. Rev.* 74:230–231, 1948.

Fou, AC, et al.: "Molecular–Level Control in the Deposition of Ultrathin Films of Highly Conductive, In–Situ Polymerized P–Doped Conjugated Polymers," *Mater. Res. Soc. Symp. Proc.* 328:113–118, 1994.

Swager, TM; Marsella, MJ: "Conducting Polymers With Chemically Sensitive Traps and Barriers: New Molecule–Based Sensors," *Mat. Res. Soc. Symp. Proc.* 328:263–266, 1994.

Ikariyama, Y; et al.: "Electrochemical Fabrication of Amperometric Microenzyme Sensor," *J. Electrochem. Soc.* 136(3):702–702, 1989.

Kent, SL; et al.: "Morphology, Chain Folding and C–LC Transitions in Liquid Crystal Polymer Single Crystals. In: Crystallization of Polymers," Dosiere, M; ed. *Kluwer Academic Publishers*; Dordrecht, Boston, London; 1993; pp. 177–188.

Albrecht, C; et al.: "The Crystallization Behavior of Rod–Like Macromolecules In: Crystallization of Polymers," Dosiere, M; ed. *Kluwer Academic Publishers*; Dordrecht, Boston, London; 1993; pp. 323–330.

Freidzon, YS; Shibaev, VP: Chap. 7. "Liquid–Crystal Polymers," Plate, NA; ed. *Plenum Press*; New York, London; 1993; pp. 251–302.

Moller, HJ: "Semiconductors For Solar Cells," *Artech House, Inc.*; Boston, London; 1993.

Green, MA: "Solar Cells. Operating Principles, Technology, and System Applications," *Prentice–Hall, Inc.*; Englewood Cliffs, New Jersey; 1982.

Fonash, SJ: "Solar Cell Device Physics," *Academic Press*; New York, London, Toronto, Sydney, San Francisco; 1981.

Bardeen, J; Cooper, LN; Schrieffer, JR: "Microscopic Theory of Superconductivity," *Phys. Rev.* 106:162–164, 1957.

Reed, MA; Seabaugh, AC: Chap. 2. "Molecular and Biomolecular Electronids," Birge, RR; ed. *American Chemical Society*; Washington, DC.; 1994; pp. 14–42.

Johnson, KW: "Reproducible Electrodeposition of Biomolecules for the Fabrication of Miniature Electroenzymatic Biosensors," *Sensors and Actuators* B5:85–89, 1991.

Degani, Y and Heller, H.; "Direct Electrical Communications between Chemically Modified Enzymes and Metal Electrodes. 2. Methods for Bonding Electron–Transfer Relays to Glucose Oxidase and D–Amino–Acid Oxidase," *J. Am. Chem. Soc.* 1988, 110, 2615–2620.

Meade, TJ: "Metal Ions in Biological Systems," Sigel, A; Sigel, H; eds. Marcel Dekker, Inc.; New York, Basel, Hong Kong; 1996; pp. 453–478.

Murphy, CJ; Arkin, MR; Jenkins, Y; Ghatlia, ND; Bossmann, SH; Turro, NJ; Barton,JK: "Long–Range Photoinduced Electron Transfer Through a DNA Helix," *Science* 262:1025–1029, 1993.

Ijiro, K and Shimomura, M: "Quantization of Double Helix DNA as Functional High Molecules," Kotai Butsuri 30(12):1042–1048, 1995. + Translation.

Stemp, EDA; Barton, JK: Chap. 11. "Electron Transfer Between Metal Complexes Bound to DNA: Is DNA A Wire? In: Metal Ions In Biological Systems," vol. 33. Probing of Nucleic Acids by Metal Ion Complexes of Small Molecules Sigel, A; Sigel, H; eds. Marcel Dekker, Inc.; New York, Basel, Hong Kong; 1996; pp. 325–365.

Gregory, BW; Stickney, JL: "Electrochemical Atomic Layer Epitaxy (ECALE)." *J.5, Electroanal. Chem.* 300:543–561, 1991.

Gregory, BW, et al.: "Conditions for the Deposition of CdTe by Electrochemical Atomic Layer Epitaxy," *J. Electrochem. Soc.* 138(5):1279–1284, 1991.

Villegas, I; Stickney, JL: "Preliminary Studies of GaAs Deposition on Au(100), (110), and (111) Surfaces by Electrochemical Atomic Layer Epitaxy," *J. Electrochem. Soc.* 139(3):686–694, 1992.

Suggs, DW;et al.: "Formation of Compound Semiconductors by Electrochemical Atomic Layer Epitaxy," *J. Vac. Sci. Technol A* 10(4):886–891, 1992.

Huang, BM; Colletti, LP; Gregory, BW; Anderson, JL; Stickney, JL: "Preliminary Studies of the Use of an Automated Flow–Cell Electrodeposition System for the Formation of CdTe Thin Films by Electrochemical Atomic Layer Epitaxy," *J. Electrochem. Soc.* 142(9):3007–3016, 1995.

Paul, EW; Ricco, AJ; Wrighton, MS: "Resistance of Polyaniline Films as a Function of Electrochemical Potential and the Fabrication of Polyaniline–Based Microelectronic Devices," *J. Phys. Chem.* 89:1441–1447, 1985.

White, HS; Kittlesen, GP; Wrighton, MS: "Chemical Derivatization of an Array of Three Gold Micorelectrodes with Polypyrrole: Fabrication of a Molecule– Based Transistor," *J. Am. Chem. Soc.* 106:5375–5377, 1984.

Kittlesen, GP; et al.: "Chemical Derivatization of Microelectrode Arrays by Oxidation of Pyrrole and N–Methylpyrrole: Fabrication of Molecule–Based Electronic Devices," *J. Am. Chem. Soc.* 106:7389–7396, 1984.

Strike, DJ; et al.: "Electrodeposition of Glucose Oxidase for the Fabrication Of Miniature Sensors," *Sensors and Actuators* B13–14:61–64, 1993.

Brown, GH; Wolken, JJ: Chap. 5. "Liquid Crystals and Biological Structures," *Academic Press*; 1979; pp. 56–72. Sci. USA 83:4581–4584, 1986.

Janata, J: "Chemical Sensors" *Anal. Chem.* 64(12):196R–219R, 1992.

Szent–Gyorgyi, A: "Internal Photo–Electric Effect and Band Spectra in Proteins," *Nature* 157:875, 1946. Szent–Gyorgyi, A: "Towards a New Biochemistry?" *Science* 93:609–611, 1941.

Szent–Gyorgyi, A: "Towards a New Biochemistry?" *Nature* 157:875, 1946. *Science* 93:609–611, 1941.

Baum, RM: "Views On Biological, Long–Range Electron Transfer Stir Debate," *Chemical and Engineering News* 71(8):20–23, 1993.

Collman, JP; et al.: "Conductive Polymers Derived From Iron, Ruthenium, And Osmium Metalloporphyrins: The Shish–Kebab Approach," *Proc. Natl. Acad. Sci. USA* 83:4581–4584, 1986.

Kanatzidis, MG: "Conductive Polymers," *Chemical and Engineering News* 68(49):36–54, 1990.

Adam, D; et al.: "Fast Photoconduction in the Highly Ordered Columnar Phase of a Discotic Liquid Crystal," *Nature* 371:141–143, 1994.

Wilson, E. K.: "DNA: Insulator or Wire?: Flurry of new research, heated debate focuses on biomolecule," *C&EN* Feb. 24, 1997. 33–39.

Keesey, J. editor and compiler: "Biochemical Information– 1st Ed. Ch. 1: Enzymes for Routine Quantitative Analysis," *Boehringer Mannheim*, 1997, pp. i– 85.

Pritchard, D., et al. "Micron–Scale Patterning of Biological Molecules," *Angew. Chem. Int. Ed. Engl.* 1995, 34, No. 1.

Yoo, M.J. et al; "Scanning Single–Electron Transistor Microscopy: Imaging Individual Charges," *Science*, vol. 276, Apr. 25, 1997.

Service, R.; Meeting Briefs; "Atomic Landscapes Beckon Chip Makers and Chemists," *Science*, vol. 274, Nov. 1, 1996.

"Science/Technology Concentrates," Sep. 12, 1994 *C&EN*, p. 19.

Caras, et al., "Field Effect Transistor Sensitive to Penicillin," 1980, *American Chemical Society*, pp., 1935–1937.

MOLECULAR WIRE INJECTION SENSORS

This is a Divisional application of Ser. No. 08/856,822 filed May 14, 1997, now U.S. Pat. No. 6,060,327.

BACKGROUND OF THE INVENTION

The present invention relates to biosensors and chemical sensors. More particularly, it relates to sensors having a chemical or biochemical species detection group connected to an electronic circuit by electrically conducting polymer strands.

Biosensors employing enzymes have been applied to the detection of numerous analyte species concentrations including glucose, cholesterol, or both glucose and cholesterol concentrations in whole blood samples. Such sensors and associated instruments employ an enzyme capable of catalyzing a reaction at a rate representative of the selected compound concentration in an assay mixture.

There are three general detection approaches employing a glucose enzyme electrode. The first and earliest measures oxygen consumption. The oxygen-sensing probe is an electrolytic cell with a gold (or platinum) cathode separated from a tubular silver anode by an epoxy casting. The anode is electrically connected to the cathode by electrolytic gel, and the entire chemical system is isolated from the environment by a thin gas-permeable membrane (often Teflon). A potential of approximately 0.8V (from solid-state power supply) is applied between the electrodes. The oxygen in the sample diffuses through the membrane and is reduced at the cathode with the formation of the oxidation product, silver oxide, at the silver anode. The resultant current is proportional to the amount of oxygen reduced. The analyzer unit operates over the range from 0.2 to 50 ppm of dissolved oxygen. Gases that reduce at 0.8V will interfere; these include the halogens and $SO_2$. $H_2S$ contaminates the electrodes.

A second approach detects $H_2O_2$ production but requires an applied potential of approximately 0.65V (from solid-state power supply) applied between the electrodes, one of which is inside a permselective membrane. The $H_2O_2$ in the sample diffuses through the permselective membrane (if one is present) and is oxidized at the anode. Many metal, metal complexes, nonmetal, organic and biochemical species that oxidize at approximately 0.65V will interfere; such as ascorbic acid, amines, hydrazines, thiol compounds, catechols, hydroquinones, ferrocenes, and metalloporphyrins. The inside permselective membrane is not always capable of removing the complicated mix of possible interferences from the analyte matrix.

A third approach takes advantage of the fact that the enzymatic reaction requires two steps. First, the enzyme glucose oxidase (GOD) (EC 1.1.3.4) is reduced by glucose, then the reduced enzyme is oxidized to its initial form by an electron acceptor, i.e., a mediator. In natural systems, the mediator is oxygen. In biosensors, another mediator compound may be employed to transfer electrons between the enzyme and a conductive surface of an electrode at a rate representative of the enzyme catalyzed reaction rate when an appropriate potential is applied to the particular redox mediator in use. Such biosensors may employ amperometric measurements to determine glucose concentration in a whole blood sample. This involves an integrated sample measurement of the area under the ampere versus time curve, corresponding to the amount of glucose in the sample.

The mechanism by which a common amperometric sensor works is depicted in FIG. 1. A sensor 2 employs glucose oxidase (GOD), for example, as a molecular recognition group. Glucose oxidase catalyzes the oxidation of glucose to gluconolactone in analyte 4. This reaction involves the $FAD/FADH_2$ redox center of the enzyme. Sensor 2 includes a molecular recognition group, region 6, attached to an electrode 8. When glucose in analyte 4 contacts GOD-FAD (glucose oxidase including the FAD redox center) in region 6, it is oxidized to gluconolactone. At the lie time, the GOD)FAD is reduced to $GOD-FADH_2$. This involves, two electrons and two hydrogen ions being transferred to the FAD. Normally, in the absence of a sensor mediator, the $GOD-FADH_2$ is reoxidized by atmospheric oxygen to GOD-FAD to complete the catalytic reaction. In the presence of a mediator, however, the $GOD-FADH_2$ is; sometimes reoxidized by a mediator (Mox). In this case, the $GOD-FADH_2$ releases two hydrogen ions to analyte 4 and two electrons to the mediator. The resulting reduced mediator ($M_{red}$) may then be reoxidized by electrode 8 at an appropriate potential. The reoxidation of the mediator is accompanied by the transfer of an electron or electrons to electrode 8. This is the current that is monitored to provide a concentration of glucose.

In theory, a mediator may be any small molecule inorganic, organometallic or organic compounds, which are reduced by the enzyme, and oxidized by an appropriate applied potential at the electrode surface. The mediator should be designed to rapidly and efficiently transfer electrons between the enzyme and the electrode. Otherwise, ambient oxygen would oxidize nearly all of the reduced GOD and the desired signal would be very weak. The mediator should also transfer a total charge proportional to the glucose or cholesterol concentration in the sample. The current which results from the mediator oxidation is known as the Cottrell current which, when integrated with respect to time, gives the number of coulombs associated with the sensor reaction. The total coulombs passed is proportional to the amount of analyte.

Unfortunately, mediators are commonly provided as mobile "reagents" which diffuse to the enzyme where they are oxidized or reduced (depending upon the reaction catalyzed by the enzyme). The oxidized or reduced mediator then diffuses to the electrode surface where it gains or loses an electron. Unfortunately, such mechanism is dependent upon the continuing presence of recycled mobile mediators. As such compounds can leak from the electrode surfaces, there may be a gradual depletion in available mediator and a consequent reduction in sensor sensitivity. Examples of diffusing redox mediators include dyes (e.g., methylene blue), ferrocene derivatives (Cass, A E G; Davis, G; Francis, G D; Hill, H A O; Aston, W J; Higgins, I J; Plotkin, E V; Scott, I D L; Turner, A P F: Ferrocene-Mediated Enzyme Electrode for Amperometric Determination of Glucose. Anal. Chem. 56:667–671, 1984), components of conducting organic metals and quinones.

Also, available sensors applying the above amperometric approach to the detection of glucose, cholesterol, lactate, $H_2O_2$, NAD(P)H, alcohol, and a variety of other compounds in whole blood samples, can have other serious complicating problems. For example, the percentage of sensor surface area covered by blood can vary: sometimes the blood sample does not cover the entire electrode. This may be caused by a poorly adherent enzyme (often applied by spraying) thus allowing leakage of blood or other analytes along the edges of the electrode. A related problem results from hydration of the reaction area prior to test. This dilutes the ligand (e.g., glucose) concentration and therefore gives a lower reading than would be accurately given by an unhydrated surface.

Further, the partial pressure of molecular oxygen ($O_2$) may complicate the interpretation of sensor data. Molecular oxygen is the natural electron acceptor mediator of the enzyme glucose oxidase (GOD). Following oxidation of D-(+)-glucose by GOD, reduced glucose oxidase ($GOD_{red}$) will transfer electrons to $O_2$ forming $H_2O_2$ in the absence of other mediators. In amperometric glucose biosensors described above, the unwanted $O_2$ side reaction competes with synthetic chemical mediators for electrons supplied by the $GOD_{red}$ enzyme. Calibration of GOD-based biosensors at different altitudes (i.e., different partial pressures of $O_2$) may be a problem if electron transfer rates of selected synthetic chemical mediators are not orders of magnitude faster than the $O_2$ side reaction.

Humidity (i.e., $H_2O$) may be another potential problem if mass action of $H_2O$ and $O_2$ present drives the enzyme catalyzed oxidation product of D-gluconolactone in reverse back to the reduced starting material, D-(+)-glucose. Catalase, a common contaminant of glucose oxidase preparations, may be driven in reverse by mass action of excess $H_2O$ and $O_2$ producing 2 moles of $H_2O_2$. $H_2O_2$ buildup combined with D-gluconolactone could drive the glucose oxidase reaction in reverse by mass action back to D-(+)-glucose.

Other problems associated with known amperometric sensors include, for example, (1) difficulty in fitting the Cottrell current curve (i.e., ampere-time graph), (2) sampling with enough frequency to accurately obtain the time integral of Cottrell current, (3) high applied potential at the electrode causing indiscriminate oxidation or reduction of interfering substances, and (4) complicated electronic circuits requiring potentiostat and galvinostat instrumentation.

Some of the above drawbacks of the current amperometric biosensors have been noted and analyzed (see, Schuhmann, W: Chap. 9. Conducting Polymers And Their Application In Amperometric Biosensors. In: Diagnostic Biosensor Polymers. ACS Symposium Series 556. Usmani, A M; Akmal, N; eds. American Chemical Society; Washington, D.C.; 1994; pp. 110–123). First, due to the fact that the active site of redox enzymes is in general deeply buried within the protein shell, direct electron transfer between enzymes and electrode surfaces is rarely encountered. This is especially true for enzymes which are integrated within non-conducting polymer membranes in front of the electrode surface. Hence, electron transfer is usually performed according to a 'shuttle' mechanism involving free-diffusing electron-transferring redox species for example the natural electron acceptor $O_2$ or artificial redox mediators like ferrocene derivatives (Cass, A E G; Davis, G; Francis, G D; Hill, H A O; Aston, W J; Higgins, I J; Plotkin, E V; Scott, L D L; Turner, A P F: Ferrocene-Mediated Enzyme Electrode for Amperometric Determination of Glucose. Anal. Chem. 56:617–671, 1984), osmium complexes (Heller, A: Electrical Wiring of Redox Enzymes. Acc. Chem. Res. 23(5):128–134, 1990), or quinones. Due to the necessity for the redox mediators to diffuse freely between the active sites of the enzymes and the electrode surface, these electrodes show a limited long-term stability as a consequence of the unavoidable leaking of the mediator from the sensor surface. Additionally in the case of the natural redox couple $O_2/H_2O_2$, the sensor signal is dependent on the $O_2$ partial pressure, and a high operation potential has to be applied to the working electrode giving rise to possible interferences from cooxidizable compounds. The second drawback is related to the fabrication of these sensors. The physical assembling of an enzyme membrane and an electrode is extremely difficult to automate and thus in principal incompatible with microelectronic fabrication techniques. Additionally, the miniaturization as well as the integration of individual biosensors into a miniaturized sensor array is impossible with techniques which are mainly based on the manual deposition of a droplet of the membrane-forming mixture onto the electrode surface.

Consequently, the next generation of amperometric enzyme electrodes has to be based on immobilization techniques which are compatible with microelectronic mass-production processes and easy to miniaturize. Additionally, the integration of all necessary sensor components on the surface of the electrode has to prevent the leading of enzymes and mediators simultaneously improving the electron-transfer pathway from the active site of the enzyme to the electrode surface.

In addition to amperometric mechanisms, which rely on detecting current generated from faradaic reactions, a potentiometric mechanism may be employed to sense analyte concentration. Potentiometric techniques monitor potential changes between a working electrode and a reference electrode in response to charged ion species generated from enzyme reactions on the working electrode. A very common potentiometric sensor is the pH sensor which registers changes in hydrogen ion concentration in an analyte. A microelectronic potentiometric biosensor, the Field Effect Transistor (FET) biosensor, has generated some interest. In this design, a receptor or molecular recognition species is coated on a transistor gate. When a ligand binds with the receptor, the gate electrode potential shifts, thereby controlling the current flowing through the. FET. This current is detected by a circuit which converts it to an observed ligand concentration. Observed problems with potentiometric systems include, for example, (1) slow response of the electrode (i.e., seconds), (2) complicated electronic circuits for three electrode (i.e., working, counter, and reference electrode) electrochemical systems requiring potentiostat instrumentation, (3) low sensitivity, and (4) limited dynamic range.

Recently, two groups (Heller et al. and Skotheim et al.) have explored and developed redox polymers that can shuttle electrons from the enzyme to the electrode. The groups have "wired" the enzyme to the electrode with a long redox polymer having a dense array of electron relays. Each relay is a redox site bound to the polymer backbone. Electrons move along the polymer by hopping from one redox appendage to the next. The polymer penetrates and binds the enzymes, and is also bound to the electrode.

Heller et al. have conducted work on Os-containing redox polymers. They have synthesized a large number of such Os-containing polymers and evaluated their electrochemical characteristics (Gregg, B A; Heller, A: Redox Polymer Films Containing Enzymes. 1. A Redox-Conducting Epoxy Cement: Synthesis, Characterization, and Electrocatalytic Oxidation of Hydroquinone. J. Phys. Chem. 95:5970–5975, 1991). Their most stable and reproducible redox polymer is a poly(4-vinyl pyridine) to which $Os(bpy)_2Cl_2$ has been attached to ⅙th of the pendant pyridine groups. The resultant redox polymer is water insoluble. To make it water soluble and biologically compatible, Heller et al. have partially quaternized the remaining pyridine pendants with 2-bromoethyl amine. The redox polymer is water soluble and the newly introduced amine groups can react with a water soluble epoxy e.g., polyethylene glycol diglycidyl ether and GOD to produce a cross-linked biosensor coating-film. Such coating-films produced high current densities and a linear response to glucose up to 600 mg/dL (U.S. Pat. No. 5,262,035 to Gregg et al.).

Heller describes the electrical wiring of redox enzymes for use as amperometric biosensors (Heller, A: Electrical Wiring of Redox Enzymes. Acc. Chem. Res. 23(5):128–134, 1990). The Heller approach is an improvement over amperometric enzyme electrodes based on diffusing redox mediators, including dyes, ferrocene derivatives, components of conducting organic metals, and quinones, all described above. In the Heller approach, redox centers of a redox polymer polycation (e.g., 2[Os-(2,2'-bipyridine)$_2$(poly (vinylpyridine))Cl]$^{1+\frac{1}{2}+}$) are electrostatically and covalently bound to the enzyme and relays electrons to the electrode, on which a segment of the polycation is adsorbed. Binding of the redox polymer polycation to the electrode can be electrostatic when the electrode has a negative surface, charge.

Fluctuations in current with partial pressure of oxygen (e.g., oxygen concentration in blood), depend on tho ratio of the rate of direct electroxidation of the FADH$_2$ centers to their rate of oxidation by molecular oxygen, and therefore on the rate of electron transfer to, and then electrical resistance of, the three-dimensional wired-enzyme structure. At high osmium-complex, concentrations, and in sufficiently thin layers, the competition is won by electron transfer to the electrode via the osmium centers, and the electrodes are relatively insensitive to oxygen (Heller, A: Electrical Wiring ofRedox Enzymes. Acc. Chem. Res. 23(5):128–134, 1990. Gregg, D A; Heller, A: Cross-Linked Redox Gels Containing Glucose Oxidase for Amperometric Biosensor Applications. Anal. Chem. 62:258–263, 1990. Surridge, N A; Diebold, E R; Chang, J; Neudeck, G W: Chap S. Electron-Transport Rates In An Enzyme Electrode For Glucose. In: Diagnostic Biosensor Polymers. ACS Symposium Series. 556. Usmani, A M, Akmal, N; eds. American Chemical Society; Washington, D.C.; 1994; pp. 47–70).

Electrodes based on conducting polypyrroles with ferrocenes also have been reported (Hale, P D ; Inagaki, T; Karan, H I; Okamoto, Y; Skotheim, T A: A New Class of Amperometric Biosensor Incorporating a Polymeric Electron-Transfer Mediator. J. Am. Chem. Soc. 111(93) 3482–3484, 1989).

Skotheim et al. have used flexible polymer chains to act as relays. Their polymers provide communication between GOD's redox centers and electrode. No mediation was found when ferrocene was attached to a non-silicone backbone. Their ferrocene-modified siloxane polymers were said to be stable and non-diffusing (Boguslavsky, L I; Hale, P D; Skotheim, T A; Karan, H I; Lee, H S; Okamoto, Y Novel Biosensors For Specific Neurotransmitters Based On Flavoenzymes And Flexible Redox Polymers. Polyl. Mater. Sci. Eng. 64:322–323, 1991).

Unfortunately, the redox polymer systems of Heller et al. and Skotheim et al. have a limited electron transfer rate based on electron hopping between dense electron relay pendant groups. Further, their "wire" redox centers must be designed to undergo reaction at a potential close to that of the enzyme catalyzed reaction. The closer the potential is to the redox potential of the enzyme itself, the lesser the likelihood that a potentially interfering substrate will be spuriously oxidized. Unfortunately, to address this issue limits the range of polymer redox couple and molecular headgroup combinations.

A fundamental presupposition for the construction of reagentless amperometric enzyme electrodes is the design of a suitable electron-transfer pathway from the active site of the enzyme to the electrode surface. According to Marcus theory (Marcus, R A; Sutin, N: Electron Transfers In Chemistry And Biology. Biochim. Biophys. Acta 81 1265–322, 1985) a redox mediator with a low reorganization energy after the electron transfer has to be able to penetrate into the active site of the enzyme to shorten the distance between the prosthetic group (e.g., FAD/FADH$_2$) and the mediator. Hence, the rate constant of the electron-transfer reaction can be increased. After this 'first' electron transfer the redox equivalents have to be transported to the electrode surface via mechanism having a rate constant which is in the range of the turnover rate of the enzyme. In the shuttle mechanism mentioned above (having mobile mediators), the electron transport involves diffusion of redox mediators. In the "wired" redox polymer sensors described above, electron transport involves hopping from one redox center to the next on the polymer backbone.

In a recent study, Aizawa et al. discuss a reversible electron transfer between the prosthetic group of pyrrolo quinoline quinone (PQQ) enzyme (fructose dehydrogenase) and all electrode through a molecular interface (Aizawa, M; Khan, G F; Kobatake, E; Haruyama, T; Ikariyama, Y: Chap. 26. Molecular Interfacing of Enzymes on the Electrode Surface. In: Interfacial Design and Chemical Sensing. ACS Symposium Series 561. Mallouk, T E; Harrison, D J; eds. American Chemical Society, Washington, D.C., 1994, pp. 305–313). The PQQ moieties of randomly oriented fructose dehydrogenase (FDH) which are very close to tile transducer electrode can easily transfer their electrons to the electrode (Shinohara, H; Khan, G F; Ikariyama, Y; Aizawa, M: Electrochemical Oxidation and Reduction of PQQ Using a Conducting Polypyrrole-Coated Electrode. J. Electroanal. Chem. 304:75–84, 1991. Khan, GF; Shinohara, H; Ikariyama, y; Aizawa, M: Electrochemical Behaviour of Monolayer Quinoprotein Adsorbed on the Electrode Surface. J. Electroanal Chem. 115:263–273, 1991). However, the prosthetic groups of FDH located far from the electrode can not provide their electrons, as the distance from the electrode exceeds the maximum electron transfer distance (~25 Å). Therefore, to make the FDH (EC 1.1.99.11, MW: 141,000) on the electrode surface electrochemically active, Aizawa et al. introduced an ultrathin conductive polypyrrole (PP) membrane as a molecular interface as "wiring" to assist the electron transfer from PQQ to the electrode. Unfortunately, the wiring used by Aizawa is randomly oriented and does not necessarily present enzyme at optimal position with respect to the analyte.

What is needed is an improved sensor design that rapidly transfers electrons from headgroup redox reactions to an electrode, does not rely on a redox relay such as freely diffusing mediators, and optimally orients the headgroup with respect to the analyte.

A great number of approaches for microfabrication of chemical sensors are currently under way, particularly in the areas of field effect transistor (FET-)based chemical sensors, metal oxide gas sensors, and biosensors. Since Janata et al. first reported micro-enzyme electrodes based on FET (Caras, S; Janata, J: Field Effect Transistor Sensitive to Penicillin. Anal. Chem. 52:1935–1937, 1980), a number of groups have been employing microfabrication techniques (e.g., photolithography) such as those employed in semiconductor device technology to fabricate micro-enzyme electrodes. Despite enormous efforts of many groups, the PET-based micro-enzyme electrodes of practical use have not been realized yet, largely because of the problems associated with potentiometric methods general lack of a fast response, high sensitivity, and wide, dynamic range.

For the construction of reagentless enzyme electrodes (e.g., electrodes analogous to those of Heller et al. and Aizawa et al.) one has to focus on a technique for the modification and functionalization of electrode and even micro-electrode surfaces to allow the strong binding of the enzyme and the redox mediator taking into account the presuppositions for an effective and fast electron transfer between the enzyme and the electrode. These features requirements are in principle met with enzyme electrodes based on redox-sensitive hydrogels, however, the manual deposition of these hydrogels is not compatible with mass-production techniques.

The electrochemical deposition of conducting-polymer layers occurs exclusively on die electrode surface and can hence be used for the immobilization of enzymes either covalently using functionalities on the polymer film or physically entrapped within the growing polymer film. As the conducting-polymer film itself does not participate in the electron transfer, mediator-modified enzymes entrapped within a polypyrrole layer have been used for the construction of a reagentless oxidase electrode.

Electrochemical deposition methods of the prior art typically use high current density and voltage potential conditions which destroy the orderly Helmholtz double-layer at the electrode surface (U.S. Pat. No. 5,215,631 to Westfall). Resulting disorderly depositions at electrode surfaces produce random polymer structures which lack orientational and positional order. Aizawa et al. "wired" PQQ-FDH in their sensors with ultrathin conductive polypyrrole (PP) membrane as a molecular interface. Electrochemical synthesis of molecular-interfaced FDH on Pt electrode was prepared by the following two steps: (1) potential controlled adsorption of FDH, and (2) electrochemical polymerization of polypyrrolo. These steps employ high voltage and current density electrochemical deposition conditions to produce polymer (FDH and polypyrrole) depositions on the Pt electrode that are randomly oriented. Therefore, this device must operate at high (~400 mV) operating potential resulting in possible interfering cooxidizable species.

What is needed is an improved technique for depositing molecular recognition groups and associated wiring, if necessary, that provides a strong direct connection between an electrode; and the molecular recognition groups, and allows the molecular recognition groups to be aligned in a common orientation.

SUMMARY OF THE INVENTION

In one aspect, the present invention provides a sensor for sensing the presence of an analyte component without relying on redox mediators. This sensor may be characterized as including the following elements: (a) a plurality of conductive polymer strands each having at least a first end and a second end and each aligned in a substantially common orientation; (b) a plurality of molecular recognition headgroups having an affinity for the analyte component and being attached to the first ends of the conductive polymer strands; and (c) an electrode substrate attached to the conductive polymer strands at the second ends.

The polymer strands in a common orientation resemble liquid crystals. Preferably, the strands are oriented substantially orthogonal to the electrode substrate. The conductive polymer strands may be, for example, one or more of multi-stranded nucleic acids, electron transport proteins, synthetic organic and inorganic conducting polymers, metal crystallite molecular wires, and Langmuir-Blodgett conducting films. In a particularly preferred embodiment, the conductive polymer strands are double-stranded DNA strands.

The headgroup may participate in a redox reaction when contacting a molecule of the analyte component. When this is the case, a mobile charge carrier is transferred directly to a conductive polymer strand attached to the headgroup, without participating in a redox reaction in the polymer strand. In one embodiment, the molecular recognition headgroups participate in the redox reaction by catalyzing a chemical transformation of the analyte component. Examples of such headgroups include oxidoreductases and catalytic antibodies. In one specific example u!;ed repeatedly in this specification, the headgroup is glucose oxidase.

The sensor headgroups may be chemically homogeneous (e.g., they are all glucose oxidase) or chemically inhomogeneous (e.g., they include a mixture of glucose oxidase, cholesterol oxidase, and cholesterol esterase). In one preferred embodiment, when the headgroups are inhomogeneous, the sensor includes a first region on the electrode substrate where a first group of chemically homogeneous molecular recognition headgroups is located and second region on the electrode substrate where a second group of chemically homogeneous molecular recognition headgroups is located The first and second regions may be separately addressable so that information signal from the two regions may be separately processed and able to indicate whether cholesterol, glucose, or both cholesterol and glucose are present in the analyte for example.

The electrode substrate should be capable of reporting to an electronic circuit reception of mobile charge carriers from the conductive polymer strands. In one specific embodiment, the electrode substrate is a diode such as a photovoltaic diode. More generally, the substrate may be a device element of a device on semiconductor chip (e.g., a gate on an FET).

In a variation of this aspect of the invention, a sensor is provided to detect the presence of a nucleic acid sequence (at a crime scene for example). The sensor includes (a) a plurality of sequence-specific single-stranded nonconductive nucleic acid wires each having at least a first end and a second end; and (b) an electrode substrate attached to sequence-specific single-stranded nonconductive nucleic acid strands at the second ends and capable of reporting to an electronic circuit, reception of mobile charge carriers originating from complementary multi-stranded nucleic acid strands. In this embodiment, when the sensor is exposed to an analyte having the complementary nucleic acid sequence, at least some of the affixed single-stranded nonconductive nucleic acid wires hybridize or anneal with the analyte to form conductive multi-stranded nucleic acid strands. Thus, charge carriers can be transported to the electrode substrate for detection. In one embodiment, the plurality of sequence-specific single-stranded nonconductive nucleic acid strands are attached to molecular recognition headgroups such that mobile charge carriers are transferred directly through only annealed multi-stranded nucleic acid strands when a redox reaction occurs at the attached molecular recognition headgroups.

Another aspect of the invention provides method of detecting a concentration of an analyte component in an analyte with a sensor having a structure as described above. The method may be characterized as including the following steps: (a) contacting the molecular recognition headgroups with the analyte; and (b) determining whether electrons have been transferred to the electrode substrate resulting from electrons generated by the redox reaction and transferred by the conductive polymer strands to the electrode substrate. When the redox reaction occurs at a headgroup, a mobile charge carrier is transferred directly to a conductive polymer strand attached to the headgroup, without redox reaction in the polymer strand. The method may further involve (c) monitoring a change in an electronic circuit connected to the electrode substrate, the change resulting from reception of mobile charge carriers from the conductive polymer strands; and (d) correlating the change in the electronic circuit with the concentration of the analyte component Another important aspect of the claimed invention is a sensor employing a diode, preferably a photodiode. Sensors in accordance with this aspect of the invention may be characterized as including the following features: (a) a plurality of molecular recognition headgroups having an affinity for the analyte component and participating in a redox reaction when contacting a molecule of the analyte component such that when the redox reaction occurs at a headgroup, a mobile charge carrier is generated; (b) a diode having a first electrode to which the plurality of molecular recognition headgroups are affixed such that mobile charge carriers generated by the redox reaction are transferred to the first electrode; and (c) a circuit for detecting when the mobile charge carriers are transferred to the first electrode. In a preferred embodiment, the plurality of molecular recognition headgroups are attached to a p-type side of the diode. Also the diode may be a device on semiconductor chip including a plurality of devices.

In a further preferred embodiment, the headgroups are attached through conductive polymer strands arranged as described in the above embodiments. Thus, for example, the conductive polymer strands may be substantially commonly oriented (e.g., orthogonal to the diode surface).

A diode sensor as described above may be used according to a method as follows: (a) contacting the molecular recognition headgroups with the analyte; (b) specifying a baseline electrical signal that is present when (i) a stimulus is provided to the diode and (ii) the plurality of molecular recognition headgroups are substantially free of the analyte component: and (c) detecting a deviation from the baseline electrical signal, which deviation results from transfer of the mobile charge carriers to the first electrode when the analyte component comes in contact with the molecular recognition headgroups. The method may further include (d) determining an amplitude of the deviation; and (e) determining an analyte component concentration directly from the amplitude of the deviation without the use of any other information from the electrical signal. It has been found that the analyte component concentration is sometimes proportional to the amplitude of this deviation. Depending upon the type of signal detector employed, the baseline electrical signal and the deviation from the baseline electrical signal may be measures of voltage or electrical current. Preferably, though not necessarily, the diode is a photovoltaic diode and the stimulus provided in the specifying a baseline electrical signal is radiant energy.

Yet another aspect of the present invention is method of forming a sensor capable of sensing the presence of an analyte component. This method may be characterized as including the following: (a) contacting a sensor substrate (e.g. a device element of a device on semiconductor chip) with a first medium containing mobile conductive polymer strands or precursors of the conductive polymer strands; (b) applying a first potential to the substrate sufficient to form a first structure having the conductive polymer strands affixed to the substrate; (c) contacting the sensor substrate, with affixed conductive polymer strands, with a second medium containing mobile molecular recognition headgroups; and (d) applying a second potential to the substrate sufficient to affix the molecular recognition headgroups to the affixed conductive polymer strands. This process produces a sensor structure in which the substrate affixed to the conductive polymer strands and the molecular recognition headgroups also affixed to the conductive polymer strands.

Preferably, the step of applying a first potential is performed at a potential which causes the affixed conductive polymer strands to be oriented in a substantially common direction. This potential may be between about 0.001 and 500 mV, for example. The step of applying a second, potential is preferably performed at a potential which causes the affixed molecular recognition headgroups to be oriented in a substantially common direction. This second potential may be between about 0.001 and 500 mV. Preferably, though not necessarily, the first medium is removed from the sensor substrate following the step of applying a first potential. In an alternative embodiment, the second medium is obtained from the first medium by performing the step of applying a first potential.

If a sensor having separated regions of different headgroups is to be created, the method may also require isolating a region of the sensor substrate prior to the step of contacting the sensor substrate with a second medium, such that the molecular recognition headgroups air deposited only in the isolated region. To produce multiple headgroup regions, the steps of isolating a region, contacting the sensor substrate with a second medium, and applying a second potential to the substrate are performed a second time. The step of contacting the sensor substrate with a second medium for a second time employs a second molecular recognition headgroup, to form a structure having a first region on the sensor substrate having a first group of chemically homogeneous molecular recognition headgroups and a second region on the sensor substrate having a second group of chemically homogeneous molecular recognition headgroups.

Sensors of this invention provide analyte concentration readings, fast responses, high sensitivity, high dynamic range, and few erroneous readings. In a glucose sensor of this invention, glucose concentration is accurately read despite changes in partial pressure of $O_2$, atmosphere, altitude, humidity, or sample application of blood. Specifically, the direct wired enzyme sensors of the present invention overcome the difficulty caused by molecular oxygen reoxidizing a reduced enzyme before that enzyme (or more precisely its redox center) can release electrons to the electrode. This is because the directly wired sensors of this invention ray provide electron transfer rates many orders of magnitude faster than enzymatic reaction rates, and electron transfer rates of diffusional redox mediators such as $O_2$ and other artificial mediators. This provides sub-millisecond digital output from the sensing chip.

Chips based on device molecular transistors may be reusable, disposable, reagentless, membraneless. Further, they are amenable to miniaturization and mass production, do not require complicated three electrode systems (i.e., no working, counter, or reference electrodes) and associated electrochemical instrumentation (i.e., no galvinostat or potentiostat), and provide real-time digital output directly from the chip.

These and other features and advantages of the present invention will be described in ore detail below with reference to the drawings.

DETAILED DESCRIPTION OF THE PREFERRED EMBODIMENTS

I. Overview

II. Solid Substrate

Figure 1:
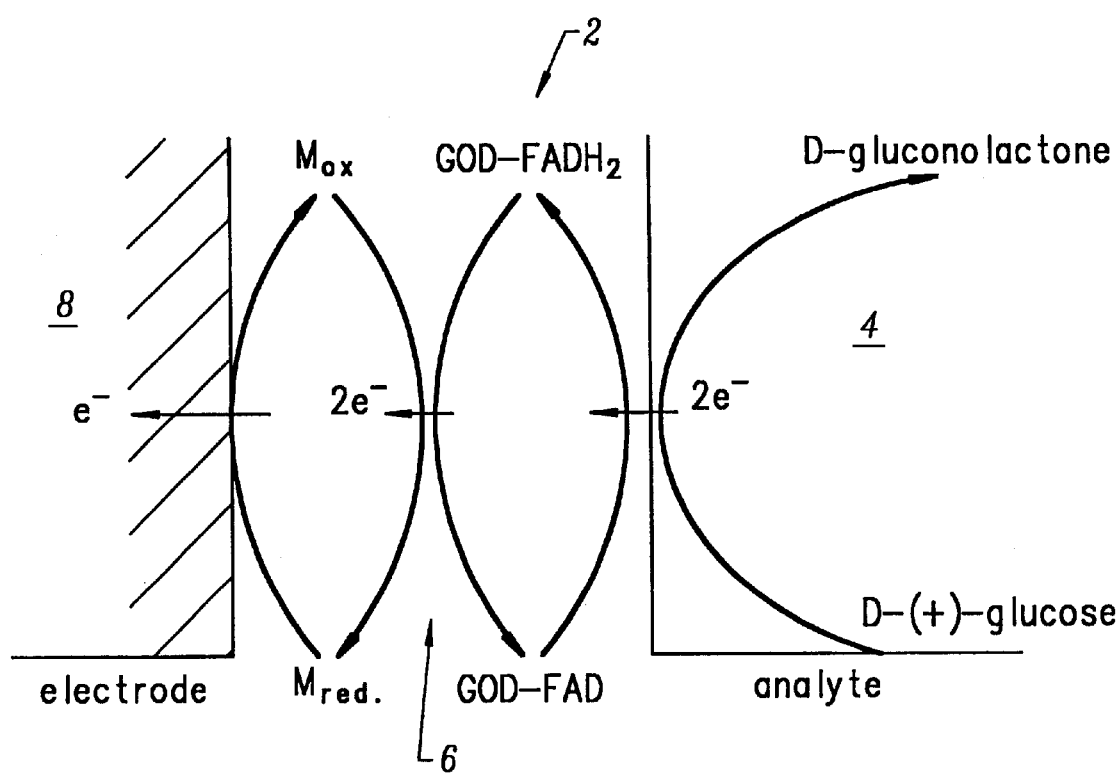
FIG. 1 is a representation of the mechanisms employed in a conventional redox mediator based biosensor.

III. Sequential Electrochemical and Chemical Deposition Techniques
A. Electrochemical Atomic Layer Epitaxy (ECALE)
B. Sequential Monolayer Electrodeposition (SMED)
C. Thin Film Chemical Deposition (CD)
D. Electrochemical Molecular Layer Epitaxy (EMOLE)
  1. Deposition of Uniaxially Oriented Liquid Crystal Conducting Biopolymers (Proteins and DNA)

IV. Conducting Polymers and Thin Films
A. Electron Transport Proteins
B . DNA Quantum Wires V. Molecular Recognition Surfaces
A. Oxidoreductases (Redox Enzymes)
B. Immunoglobulins VI. Conduction Mechanisms through Polymers on Solid Substrates
A. Energy Bands in Uniaxially Oriented Liquid Crystal Conducting Biopolymers (Proteins and DNA) and Semiconductor Substrates
B. Superconductivity VII. Applications VIII. Screening and Assays IX. Examples I. Overview The present invention relates to sensors, sensor fabrication processes and semiconductor devices that include the sensors. The sensors and related devices may be used for recognizing the presence of, quantitating the amount of, and/or continuously monitoring the level of, one or more selected components in a solid, semi-solid, liquid, or gas mixture. Preferably, an active molecular recognition surface is "hard wired" to the substrate surface (e.g., a semiconductor surface) by an oriented liquid crystal wire that is itself conductive. The molecular recognition surface may be of biologically active material of the type conventionally employed in sensors. The substrate may be patterned or unpatterned and may include (particularly when semiconductors are involved) a conductive coating such as a metal between the underlying bulk substrate and the liquid crystal wire.

Hard wiring as that term is used herein may be achieved, in one embodiment, via electrochemical fabrication methods described in detail below. Generally, such methods male use of low-cost, rapid-prototyping sequential electrochemical and chemical deposition techniques such as electrochemical molecular layer epitaxy (EMOLE) which perform "molecular wiring" aid "molecular soldering" procedures. The liquid crystal wiring arrangement preferably provides a "lawn" of commonly oriented "molecular devices" each including a single molecular recognition site "headgroup" and attached molecular wire "tail." For context, each such device might range in size from about ~2 to 2500 $Å^2$ surface area (e.g., enzyme, enzyme co-factor, substrate, supramolecular assembly, cavitand, host-guest complex, ligand, receptor, antibody, antigen, etc.).

Biosensors of the present invention may require very low operating potentials. In a preferred embodiment, extended conformation of straight uniaxially oriented liquid crystal DNA wires are stuck into the GOD active site/redox center of the prosthetic group $FAD/PADH_2$, to provide an electron transfer pathway to the surface of a p-n homojunction on semiconductor solar cell substrate. A pair of electrons per enzyme turnover event injected from the wires combine with a pair of holes in the p-type semiconductor layer, interfering with the normal photocurrent (i.e., electron/hole pair recombination) occurring in the solar cell. The oriented liquid crystal enzyme (molecular recognition headgroup) and attached oriented liquid crystal DNA wire tail constitute a molecular transistor. The device communicates with a solid substrate (i.e., p-n homojunction) through the uniaxially oriented liquid crystal DNA wire tail interconnects. One end of the DNA wire is stuck in the oriented liquid crystal enzyme active site/redox center and the other end is stuck into the p-type semiconductor layer providing a direct connection between the protein enzyme, DNA, and semiconductor substrate.

In general, the sensors of this invention may be categorized used upon their transduction and/or gating mechanisms of the headgroup(s): switched or gated by optical (optoelectronic), chemical (chemoelectronic), magnetic (magnetoelectronic), radioactive (radioelectronic), thermal (thermoelectric), mechanical (piezoelectric), or electrical (voltage, current, resistivity, capacitance).

Figure 2:
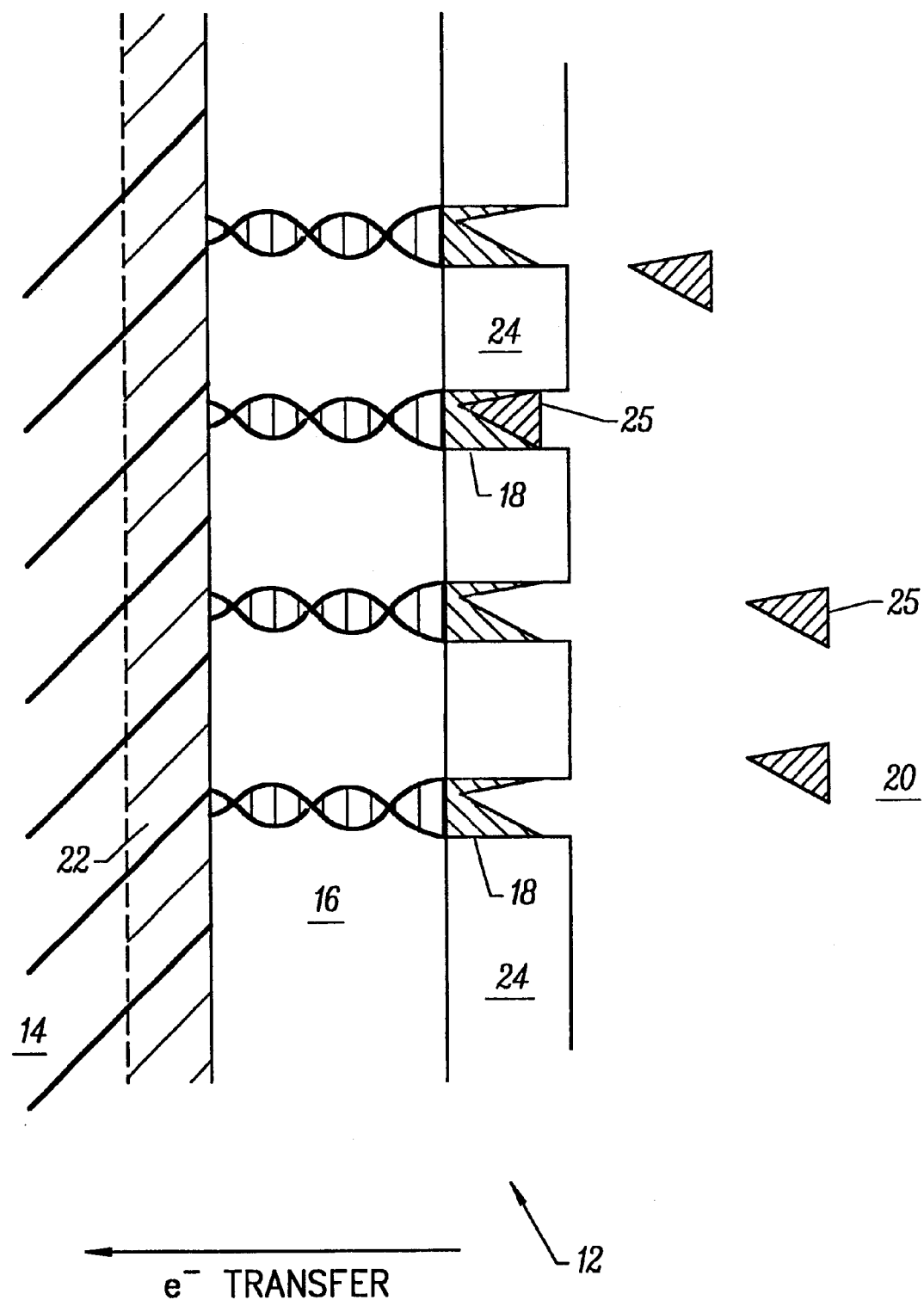
FIG. 2 is a representation of a sensor-solution interface in accordance with this invention and showing a substrate, molecular wire, and molecular recognition headgroup.
Figure 3:
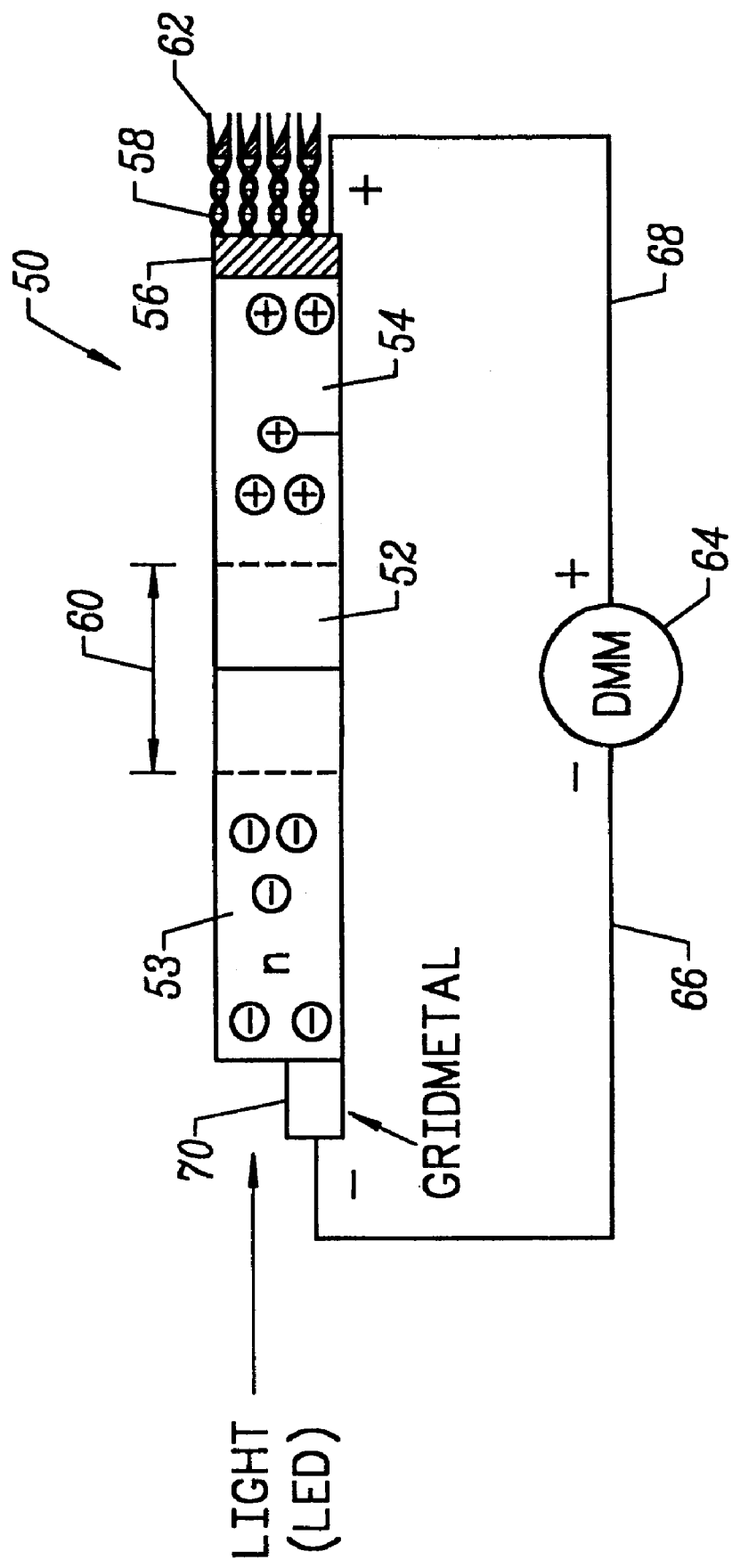
FIG. 3 is a schematic illustration of photodiode sensor in accordance with an embodiment of the present invention.

FIGS. 2 and 3 depict sensors structures in accordance with certain preferred embodiments of the present invention. FIG. 2 presents a cross-sectional view of a surface. region of a sensor 12. As shown, sensor 12 includes an electrode 14 which is preferably made from silicon or another semiconductor substrate. Attached to electrode 14 is a plurality of conducting polymer strands 16. In a preferred embodiment, each strand is a DNA double-stranded molecule. Conductive polymer strands 16 are orientated substantially in a common direction which is shown to be normal (orthogonal) to substrate 14. Strands 16 are coupled to substrate 14 in a manner that allows direct electrical influence between these two features in the sensor. For example, the connection night allow electrons to be directly transferred from strands 16 to substrate 14 so that circuitry coupled to substrate 14 can detect injection of electrons. In addition, a potential applied to substrate 14 may influence the physical state of conductive polymer strands 16.

As will be described in more detail below, a preferred process for affixing polymer strands 16 to substrate 14 provides this direct electronic coupling and in addition orients the strands 16 along a substantially common axis. Because strands 16 are oriented in a substantially common direction, they will sometimes be collectively characterized herein as a liquid crystal.

Note that liquid crystal conductive polymer strands such as those shown in FIG. 2 take the form of a "lawn" having first ends attached to molecular recognition headgroups 18 and second ends attached to electrode 14. As will be described below, headgroups 18 may take many different forms. Generally, they should change physical or chemical state in response to the presence of a particular component in analyte 20. In a preferred embodiment, molecular recognition headgroups 18 are enzymes which undergo a redox transformation in response to contact with a specified analyte component. For example, the analyte may include a ligand or substrate component 25 which selectively binds with and is chemically modified by headgroups 18. Preferably, the chemical modification is accompanied by generation of electrons which can directly transferred to strands 16 and from there to electrode 14. Depending upon the type of molecular recognition headgroup 18 employed in the sensor 12, the thickness of a headgroup layer on top of the conductive polymer lawn 16 may be between about 5 and 150 angstroms.

Importantly, no mediator is required in this sensor design, so electron transfer is direct and fast from headgroup 18 to electrode 14. Further, because the polymer strands 16 are commonly oriented, headgroups 18 are optimally presented for sensing the desired analyte component. That is, headgroups 18 are not sterically hindered by polymer strands 16 of others structures.

While the plurality of conductive polymer strands 16 may have a rather uniform length as depicted in FIG. 2, this need not be the case. More frequently, the individual polymer strands will have a wide range of lengths. This will be due to inherent variations in polymerization techniques or the polymer shearing techniques. Of course, the distribution of polymer strand lengths can be made more uniform by passing a raw collection of polymer strands through a chromatography column, electrophoretic gel, ultrafiltration membrane, or other sizing apparatus. In a preferred embodiment, the average strand length of conductive polymer strand 16 is between about 2 and 1,000 Å. More preferably, the length is between about 10 and 100 Å, and most preferably between about 3 and 40 Å. When DNA is employed as the conductive strands, the width of the individual sensor strands is in the neighborhood of 20 Å.

In a preferred embodiment, the substrate 14 is a p-type electrode of a silicon photodiode. It may include, though this is not always necessary, a metallic back plate 22 for providing an ohmic contact between polymer strands 16 and bulk silicon electrode 14. Such back metal plates are conventionally used in semiconductor devices as terminals for connection to an external circuit. The back metal plate 22 may be made from any suitable conductive metal or alloy, including but not limited to aluminum, copper, silver, gold, and platinum. Region 24 represents the close packed liquid crystal spacing between EMOLE deposited molecular recognition headgroups. Molecular recognition headgroups whose dimensions are greater than the width of underlying molecular wires to which they are attached occupy region 24.

In a preferred embodiment, the semiconductor substrate forms part of a rectifying diode such as a photodiode. FIG. 3 provides a schematic illustration of a photodiode based biosensor in accordance with one embodiment of the present invention. A sensor 50 includes a photodiode 52 including an n-type region 53 and a p-type region 54. Generally, any conventional photodiode may be employed with this invention, but it should have a surface suitable for affixing conductive polymer strands and molecular recognition headgroups as described above. To this end, p-type region 54 may be provided with or without a back metal ohmic contact 56 as shown. A plurality of strands of conductive polymer 58 are affixed at one end to back-metal plate 56. The other ends of polymer strands 58 are attached to a collection of molecular headgroups 62. The resulting structure, as illustrated, may be identical with the structure of elements 14, 22, 16 and 18 as shown in FIG. 2.

Photodiode 52 includes a depletion region 60 which automatically forms at the p-n semiconductor junction. As is known to those of skill in the art, depletion regions form at these interfaces because mobile holes diffuse from p-type regions into n-type regions just across the interface where they are combined with electrons available in the n-type region. Similarly, mobile electrons in the n-type region diffuse across the interface to the p-type region where they combine with holes. As a result, within the reach of charge carrier diffusion, essentially all mobile charge carriers are depleted.

When light (or other radiant energy of appropriate wavelength) is shown on a photodiode such as photodiode 52, some holes and electrons cross the semiconductor band gap and provide additional mobile charge carriers which can be drawn out of photodiode 52 by an applied potential or external short circuit connection. Applied potentials or external short circuit connections may be made through a digital multi-meter 64, a variable potential power supply, a battery, another photodiode, or a potentiostat, for example. Of course, many other potential sources or external short circuit connections may be employed. A multi-meter 64 has the advantage of being inexpensive yet able to detect the amount of current flowing as a result of the incident light. Additional electrons are attracted to p-type region 54 by the excess holes generated by the light. Similarly, electrons flow out of n-type region 53 because there are now excess electrons by virtue of the light excitation. This current flows through a line 66, multi-meter 64, and a line 68. Note that line 68 is electrically connected to back plate 56. Similarly, line 66 is connected to a metal back plate 70.

When electrons are injected into the p-type region 54, they may combine with and thereby annihilate holes. Thus, the photocurrent amplitude is reduced. Detection of this deviation from normal photocurrent specifies that an analyte component has been detected. It has been found that the amplitude of this deviation is proportional to the analyte component concentration. Further, it has been found that the deviation is present in both the current and voltage associated with the photodiode.

It should be understood that the sensors of this embodiment of the invention can be formed on any type of diode in which an external stimulus generates a baseline current. Such stimulus may be heat (thermally generated charge carriers), electric field, radiation, etc. In each case the baseline current is at least partially "quenched" by electrons or holes injected from the lawn of molecular devices when a specified analyte component is present. Amplitude of the deviation from baseline is often proportional to concentration of the analyte component. A simple calibration curve for each chip can be used to determine concentration of the analyte component(s) in unknown samples.

In a particularly preferred embodiment, the sensor is divided into a plurality of regions, each capable of sensing the presence of a different analyte component. For example, a first region might include, as molecular recognition headgroup, glucose oxidase to sense the presence of glucose, a second region might include cholesterol esterase and cholesterol oxidase to sense the presence of cholesterol, a third region might include alcohol dehydrogenase to gene the presence of ethanol, etc. Each of these regions will be separately addressable by electronic circuitry to uniquely identify the presence a particular analyte component. Each of the sensor regions could be made separately addressable by specialized circuitry employed in conventional integrated circuits. While the circuitry need not be particularly complex, such devices allow very sophisticated processing of the data provided by the sensor regions.

The molecular devices (headgroup and conductive strand affixed to an electrode surface) in each region may be formed by processes similar to those employed in integrated circuit fabrication. For example, certain regions could be exposed to light radiation shown through a patterned reticle. Those regions would be selectively activated or protected depending upon the use of appropriate chemical protecting groups. A liquid crystal conductive polymer region or headgroup region would then be formed on the reactive regions. Such processes are described in U.S. Pat. No. 5,252,743 issued to Barrett et al. and Pritchard et al., "Micron-Scale Patterning of Biological Molecules" Angew. Chem. Int. Ed. Engl., Vol. 34, No. 1, pages 91–93 (1995), for example, which is incorporated herein by reference for all purposes. Alternatively, an electric potential could be selectively applied to certain of the substrate regions to selectively eletrodeposit the distinct sensor regions.

II. Solid Substrate

Various solid substrates may be employed in the invention. The solid substrate should undergo a detectable change in response to an electrical stimulus from the molecular wire. The substrate material may be biological, nonbiological, organic, inorganic, or of a combination of any of these, existing as particles, strands, precipitates, gels, sheets, tubing, spheres, containers, capillaries, pads, slices, films, plates, slides, etc. The substrate may have any convenient shape such as disc, square, sphere, circle, etc. The substrate and its surface preferably, though not necessarily, form a rigid support on which to carry out the reactions and fabrication processes described herein. The substrate and its surface may also be chosen to provide appropriate crystal or non-crystal lattice structure, wafer or thin film orientation, n- and p-type doped materials, surface texture, back metal pattern, grid metal pattern, surface chemistry, etc. The raw macrosolid substrate may be composed of a semiconductor or standard electrical component. Preparation of surfaces by lapping, polishing, chemical treatment, ion implantation, photolithography, etching, chemical vapor deposition (CVD), molecular beam epitaxy (MBE), etc. may provide a patterned macro-solid substrate suitable for further processing by means of the present invention.

Various semiconductor substrates may be employed in the invention. The semiconductor substrate may be biological (e.g., lipid bilayers, membranes, detergent solubilized membrane fragments containing embedded protein electron transport pathways, blood brain barrier (BBB), epithelial linings, intestinal linings, intracellular membrane fragments, intracellular organelles. different tissue cell surface types, membrane surfaces from different blood types of red blood cells, membrane surfaces from different types of lymphocytes, macrophages, and white blood cells, lyposomes, arterial and venous blood vessel walls, neuronal conduction pathways, etc.), nonbiological, organic, inorganic, or of a combination of any of these. Usually, the Semiconductor substrate will be composed of silicon, doped diamond, indium tin oxide, tin oxide, gallium arsenide, cadmium sulfide, cadmium selenide, cadmium telluride, germanium, copper indium diselenide, copper indium disulfide, copper indium ditelluride, zinc sulfide, zinc selenide, mercury telluride, mercury selenide, graphite, etc or combinations thereof. Other substrate materials will be readily apparent to those of skill in the art upon review of this disclosure. In a preferred embodiment the semiconductor substrate is a p-n doped polycrystalline or monocrystalline silicon (e.g., having a surface crystallographic orientation in the <100> or <111> direction) or copper indium diselenide monocrystalline thin film deposited onto glass.

A semiconductor substrate may form part of a homojunction device where the same semiconductor material is employed on either side of the p-n junction, differing only in dopant type; or heterojunction device, where the materials on either side of the p-n junction are semiconductors but different semiconductors. Processes and chemistries for homo- and heterojunction device manufacture are known in the art and will not be described in significant detail. A conventional photovoltaic solar cell is an example of a semiconductor homojunction device. It is a standard n-p junction, rectifying diode with contact metallization partially covering its emitter to allow light entrance.

In a rectifying diode, for example, conducting back metal contact patterns may be located on the p-type surface and conducting grid metal contact patterns may be located on the n-type surface. Such back metal patterns are generally used for the purpose of providing an ohmic contact to the semiconductor diode. In the present invention, they may be used for attaching highly conductive terminal contacts of the conducting polymer to the semiconductor substrate surface in specific regions as described in the next section. Back or grid metal contacts are typically made from a conductive metal layer such as aluminum, copper, gold, silver, etc. The back or grid metal may be textured and may adopt lattice matching of underlying monocrystalline <100> or <111> silicon surfaces upon which it is deposited. Alternatively, the conducting polymers or thin films of this invention may be directly connected to p-type polycrystalline or monocrystalline surfaces, without the need for back metal.

The raw macro-solid substrate may be connected to or comprise standard electrical components (e.g., transistor, diode, electrode, semiconductor heterojunction, semiconductor homojunction, Schottky barrier, capacitor, resistor, inductor, CMOS, TFM CMOS, FET, ISFET, MOSFET, ENFET, REFET) or combinations thereof (See e.g., U.S. Pat. No. 5,126,921 to Fujishima et al.; U.S. Pat. No. 5,108,819 to Heller et al.; U.S. Pat. No. 5,403,700 to Hollor et al.). Memory and logic circuitry on such chips can be employed to interpret sensor signals. In a preferred embodiment, the sensor wiring will be attached io transistor gates, sources, or drains (to control potential) or to other circuit or device components to control current. Preparation of active surfaces on the semiconductor substrate may be accomplished by various fabrication techniques including, for example, lapping, polishing, chemical treatment, ion implantation, photolithography, etching, chemical vapor deposition (CVD), molecular beam epitaxy (MBE), etc.

It may be possible to wire only few or even one conductive polymer strand to a device element such as gate of a FET. Using available technology reported by Yoo et al. in *Science*, entitled "Scanning Single-Electron Transistor Microscopy: Imaging Individual Charges", Vol. 276, pages 579–582 (1997) (which is incorporated herein by reference for all purposes), source, drain, and gate elements of very small dimensions have been fabricated on a scanning tunnelling microscope ("STM") tip. Such devices have been reported to detect transfer of single charge carriers. By attaching one or a few conductive polymers (and associated headgroups) to the gate of such device, for example, a single binding event (at single headgroup) could be detected. If the individual devices are made separatedly addressable, each polymer strand/headgroup combination could form a molecular transistor of very small dimensions. Separately addressable STM tips are discussed by Service in *Science*, "Atomic Landscapes Beckon Chip Makers and Chemists" Vol. 274, pages 723–724 (1996).

III. Sequential Electrochemical and Chemical Deposition Techniques

Sequential electrochemical or chemical deposition techniques may be used to attach molecular recognition surfaces to conductive polymers and to attach conductive polymers onto semiconductor wafer substrates prepared as described above. Specifically, the present process methods of this invention may employ various processes related to electrochemical atomic layer epitaxy (ECALE), sequential monolayer electrodeposition (SMED), and thin film chemical deposition (CD) in a process referred to herein as electrochemical molecular layer epitaxy (EMOLE) to deposit, polymerize, and/or orient monomers, polymers, macromolecules, or thin films into liquid crystal conducting polymers or "molecular wires" with highly conductive terminal contacts. Preferably, one terminal contact of the formed one-dimensional molecular wire is "molecularly soldered" or electrically connected to the substrate surface (i.e., the back metal coated on a p-type surface of the semiconductor homojunction substrate). The other terminal contact is directed outward by virtue of extended liquid crystal conducting polymer orientation perpendicular to the substrate surface as illustrated above in FIG. 2. Repeat of analogous deposition techniques are used to "molecularly solder" or electrically connect an active molecular recognition headgroup to the free terminal contacts (also illustrated in FIG. 2) permitting rapid and direct charge conduction from the molecular recognition sites to the semiconductor substrate.

In a preferred embodiment of the invention, sequential deposition occurs only in specific regions of the semiconductor substrate (e.g., on specific electrically or chemically activated surface regions of the substrate electrode). This provides a patterned surface of individually wired molecular recognition sites.

Examples of three sequential deposition techniques (electrochemical and chemical) and their application to production of atomic layers of compound semiconductors and conducting polymers are described below in Section III, A–C. A modified form of these processes called electrochemical molecular layer epitaxy (EMOLE) may be employed to fabricate a single sensor site or an array of sensor sites.

A. Electrochemical Atomic Layer Epitaxy (ECALE)

The epitaxial growth of semiconductors is an important and active area of research. The development of new, low temperature techniques for the preparation of high-quality semiconducting thin-film materials is of fundamental importance to the semiconductor chip industry. Considerable effort has been devoted to study the epitaxial growth of these materials in vacuum (e.g., molecular beam epitaxy (MBE). Electrodeposition represents an alternative to the expense of vacuum techniques. In addition, electrochemistry is usually performed near room temperature, and therefore avoids the interdiffusion problems associated with the high temperatures used in vacuum deposition methods. Research has been directed towards the epitaxial electrodeposition of II–VI compound semiconductors. A method for epitaxial electrodeposition and digital etching, electrochemical atomic layer epitaxy (ECALE), is being developed. The method involves the alternated electrodeposition of atomic layers of the constituent elements which make up a compound. Deposition is limited to an atomic layer by the use of underpotential deposition (UPD). UPD refers to a surface-limited process whereby a depositing element forms a compound with substrate surface atoms at a potential below that required for bulk deposition of the element. Deposition of the element proceeds until the surface is "covered". After the surface is covered, subsequent deposition requires a higher potential to promote bulk deposition. Thus, UPD is usually limited to monolayer coverage.

ALE (atomic layer epitaxy) refers to a series of vacuum based methods for semiconductor growth where a compound is formed a monolayer at a time by the alternated deposition of atomic layers of the constituent elements. ALE is applicable to a variety of thin film formation methods such as molecular-beam epitaxy (MBE), metalloorganic molecular beam epitaxy (MOMBE), chemical vapor deposition (CVD), metalloorganic chemical vapor deposition (MOCVD), etc. These vacuum methods involve such problems as the need for careful control of reactant fluxes in order to obtain epitaxial deposits. ALE is currently under development which allows less stringent control of growth parameters. Unique to ALE is compound growth of one atomic layer at a time. This technique relies on surface-specific reactions which result in only a monolayer of reactivity. If the reactant is an elemental vapor, the substance temperature is adjusted so that bulk deposits sublime while the first monolayer remains due to an enhanced stability resulting from compound formation. After pumping (evacuation) of the first element, a similar procedure is performed with the second element. For a compound such as CdTe, a layer of Cd is formed followed by a layer of Te. Thin film growth is achieved by repeating the cycle.

In the formation of a compound such as GaAs by ALE in the MOCVD mode, a flux of $H_3As$, an arsenic precursor gas, is exposed to the substrate at a temperature which allows formation of a single As surface layer. All excess $H_3As$ is subsequently pumped away under high vacuum. The As atomic layer is stabilized by compound formation with previously deposited Ga. A flux of tetramethyl gallium (TMG), a gallium precursor gas, is then exposed to the surface, and similarly an atomic layer of Ga is formed. Excess gas is pumped away under high vacuum. Thin films are produced by repeating this cycle.

ECALE is the electrochemical analog of atomic layer epitaxy, (ALE) employing UDP in place of temperature control to deposit monolayers. Use of UPD in order to electrodeposit atomic layers of both elements, at present, requires that one element be deposited by reductive UPD while the other is deposited by oxidative UPD. In this way, one underpotentially deposited element can be held on the surface at the potential used subsequently to deposit the other element. In the formation of a compound such as CdTe, Te can be oxidatively underpotentially deposited from $Te^{2-}$ at a fairly negative potential. Cadmium can next be reductively underpotentially deposited from a $Cd^{2+}$ solution at a more positive potential, where previously deposited Te remains stable. Electrodeposited semiconductors do not have to be annealed as in ALE which is typically done for 15 minutes at 300° C.

Digital etching, the reverse process of deposition, is a natural extension of the ECALE method. Increasing the negative voltage potential to strip or etch monolayers is possible. A method for the digital electrochemical etching of compound semiconductors in an electrochemical flow cell system in which alternating electrochemical potentials are applied between a reference electrode and the compound semiconductor sufficient to strip portions, preferably atomic layers, of the elements of compound semiconductors from the compound semiconductors is described in Stickney et al.: U.S. Pat. No. 5,385,651 and Stickney et al.: WO 94128203.

B. Sequential Monolayer Electrodeposition (SMED)

Sequential Monolayer Electrodeposition (SMED) provides monolayers of II–VI compound semiconductors and is related to the B(AU method described above. However, unlike the ECALE method, all deposited elements are provided in the same electroplating solution. They are codeposited and then one which deposited in excess is electrochemically stripped away. For example, $Cd^{2+\ and\ Se2-}$ may be deposited from the same electroplating solution by cyclic voltammetric deposition at fast scan rates with a nickel rotating disk electrode. The procedure was designed to eliminate the problem of bulk Se formation, using a cyclic deposition scheme that cathodically deposits submonolayer amounts of CdSe and a large stoichiometric excess of Cd. The excess Cd is then stripped off by sweeping the electrode to a positive potential as part of the voltammetry cycle (Cd is readily stripped close to its thermodynamic reduction potential). Since the CdSe phase has a large negative free energy of formation ($\Delta G°_{f,298K}$=-141.5 kJ mol$^{-1}$), it was thought that any free Se that is deposited in this process will react with the excess Cd to form CdSe and not lead to large amounts of excess Se in the film. The net result is thus the sequential deposition of stoichiometric CdSe a monolayer (or less) at a time. It has been reported that such a procedure leads to compositionally homogeneous, stoichiometric films and may be a general method to electrodeposit binary materials with large thermodynamic or kinetic stabilities. (Kressin, A M; Doan, W; Klein, J D; Sailor, M J: "Synthesis of Stoichiometric Cadmium Selenide Films Via Sequential Monolayer Electrodeposition" *Chem. Mater.* 3(6): 1015–1020, 1991).

C. Thin Film Chemical Deposition (CD)

Conducting polymers continue to look promising as the active elements of electronic and chemical devices such as flexible light-emitting diodes, chemical sensors, and photovoltaic devices. As a result, the thin film processing techniques for these materials have become increasingly important to the successful fabrication and optimization of useful all-organic thin film devices. Techniques such as spin coating, electrochemical deposition, and Langmuir-Blodgett thin film transfer have all been utilized with varying degrees of success to manipulate conjugated polymers into thin films. Fou et al. (Fou, A C; Ellis, D L;, Rubner, M F: Molecular-Level Control in the Deposition of Ultrathin Films of Highly Conductive, In-Situ Polymerized P-Doped Conjugated Polymers. Mater. Res. Soc. Symp. Proc. 328:113–118, 1994.) has described a thin film processing technique that has been developed for the fabrication of ultrathin films of conducting polymers with angstrom-level control over thickness and multilayer architecture. Molecular self-assembly of in-situ polymerized conjugated polymers consists of a layer-by layer process in which a substrate is alternately dipped into a solution of a p-doped conducting polymer (e.g., polypyrrole, polyaniline) and a solution of a polyanion. In-situ oxidative polymerization produces the more highly conductive, underivatized form of the conjugated polymer, which is deposited in a single layer of precisely controlled thickness (30 to 60 Å). The thickness of each layer can be fine-tuned by adjusting the dipping time and the solution chemistry. The surface chemistry of the substrate (i.e., hydrophobic, charged, etc.) also strongly influences the deposition, thereby making it possible to selectively deposit conducting polypyrrole onto well defined regions of the substrates.

D. Electrochemical Molecular Layer Epitaxy (EMOLE)

Electrochemical molecular layer epitaxy (EMOLE) is a processing technology used to engineer the structure and properties of macromolecules deposited on a substrate surface in order to produce highly organized molecular materials. Preferably, this processing yields liquid crystal structures of the type described above. Typically, crystallization is viewed as producing homogenous and well ordered materials made of one or a few kinds of atoms or small molecules. It is also possible though to crystallize larger and more complex molecules such as proteins, DNA, supramolecular assemblies such as ribosomes, and even virus particles with atomic masses in excess of 100 million daltons. In fact, this is a necessary step in elucidating the structure of many macromolecules. Cocrystallization of two or more different components is also possible. The present invention provides EMOLE techniques to produce layers of two-dimensional crystals or generally well ordered arrangements of interconnected macromolecules for the production of a biosensor. EMOLE as described herein generally employs low current density and potential (which maintains the Helmholtz doublelayer) to deposit uniaxially oriented liquid crystal conducting biopolymers (proteins and DNA) at substrate surfaces.

Preferably, methods of this invention employ EMOLE to deposit, attach, polymerize, and/or orient monomers, polymers, macromolecules, or thin films into liquid crystal conducting polymers or "molecular wires" with conductive terminal contacts. "Thin film" is a term used herein to mean a well defined atomic or molecular deposition layer on a flat two-dimensional substrate. Thin films can be made by many techniques (i.e., ALE, CVD, Langmuir-Blodgett, dip coating, spin coating, EMOLE, etc.) and be composed of many materials. Thin films can sometimes be characterized as a "lawn" or "liquid crystal."

Conditions which promote oriented liquid crystal polymers will be presented below. EMOLE may be employed to form conductive electronic connections at each end of the oriented liquid crystal conducting polymers (i.e., the headgroup end and the substrate end). By connecting them at a first end of conductive polymer strands in a liquid crystal orientation, the molecular recognition headgroups are sterically unhindered in their chemical or biochemical binding/recognition of analyte species. As a consequence of an analyte binding event to a molecular recognition site, rapid electron or hole transfer from the oriented liquid crystal molecular recognition site through the attached oriented liquid crystal conducting polymer or thin film, to the semiconductor substrate will produce a signal. The amplitude of the signal or number of electrons or holes tunneling to the semiconductor surface taken in aggregate will reflect the amount of specified analyte species present.

Figure 4A:
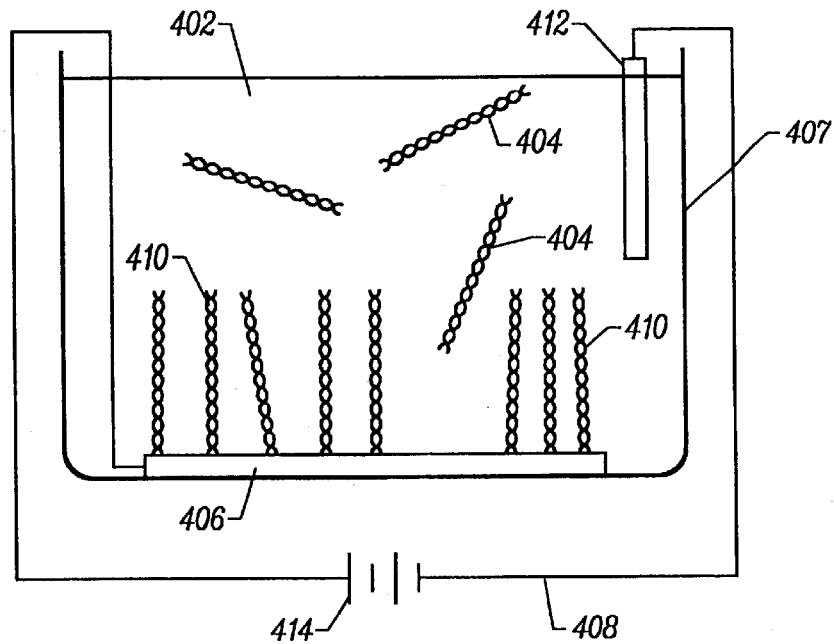
FIG. 4A is representation of an electrodeposition step for attaching molecular wires to a substrate in accordance with an embodiment of this invention.

In a preferred embodiment of this invention, a first electrodeposition cycle affixes strands of a conducting polymer on a substrate (e.g., a p-type surface of a semiconductor such, as a p-n junction solar cell described above). This is depicted in FIG. 4A. In this cycle, a first medium 402 containing a polymer 404 to be deposited (or a precursor of that polymer such as monomers) is contacted with a substrate 406. Preferably, though not necessarily, medium 402 is a liquid solubilizing the polymer strands. Medium 402 may be held within a container 407 as shown, or may passed over substrate 406 in a continuous flow reactor. A potential is then applied to substrate 406 via a circuit 408 to drive the first cycle and deposit a lawn of immobilized polymer strands 410. Note that circuit 408 includes substrate 406, medium 402, a counter electrode 412, and a power supply 414. If polymer strands 404 have a positive charge, then a negative potential is applied to the substrate; but if they have a negative charge, a positive charge is applied to the substrate. In either event, the potential and/or current density should be controlled to ensure that (1) the polymer is affixed to the substrate with strength to allow electron transport, and (2) the deposited polymer strands have a substantially common orientation. It may be desirable to include a charge group on only one end of polymers 404 so that that end is selectively coupled to the surface of substrate 406. If the polymer strand is a nucleic acid, the charge group could be attached by including it at one end of a nucleic acid strand (designed much like a conventional nucleic acid probe) which strand is complementary to an end of the nucleic acid to be affixed. Of course, other techniques for attaching charge groups (or other functional groups) to one end of a polymer strand are known in the art and may be profitably employed in the context of the present invention.

In a specific embodiment, electrodeposition current density ranging from about 10 to 300 $\mu$A cm$^{-2}$ and voltage potential ranging from about 10 to 300 mV can be generated by light induced photoconduction at the n-type and p-type surfaces of the submerged solar cell. Deposition cycle variables include i) applied potentials (i.e., magnetic/voltage); ii) solution condition (i.e., concentration of deposited material, pH, electrolyte, solvent, temperature, etc.); and iii) semiconductor substrate (i.e., polycrystalline, monocrystalline, single-crystal face orientation, smooth or textured surface, metal contact coating, lattice matching of coating, etc.). As will be understood to those of skill in the art, these variables may be adjusted to produce an optimal molecular-scale structure.

For example, the following guidelines may be employed to deposit suitable molecular wires. First, applied potentials must be low enough (e.g., 0.001 to 1500 mV) to maintain a Helmholtz double-layer during electrodesposition of conducting polymers and molecular recognition headgroups onto semiconductor substrate. Applied potential ranges will vary depending on the size, charge density, counter ion, and viscosity of the to be deposited material. Second, current densities must be low enough (e.g., 0.001 to 1500 $\mu$A cm$^{-2}$) to maintain a Helmholtz double-layer during electrodesposition of conducting polymers and molecular recognition headgroups onto semiconductor substrate. Current density ranges will vary depending on the size, charge density, counter ion, and viscosity of the to be deposited material. Third, the semiconductor substrate should be chosen to maintain a Helmholtz double-layer during electrodeposition of a uniaxially oriented liquid crystal structure on the surface of the semiconductor substrate. As noted, it may be polycrystalline or monocrystalline, having smooth or textured surface. It may also have a metal contact coating.

Further, the solution conditions should meet certain specific criteria. For example, the concentration of deposited material should be low enough (e.g., 0.001 to 10 mg/nL) to maintain a Helmholtz double-layer during electrodesposition of conducting polymers and molecular recognition headgroups onto semiconductor substrate. Further, the pH should be adjusted to approximately two (2) pH units above or below the pK$_a$ or pI of the conducting polymer or molecular recognition headgroup to produce a polymer of opposite charge from the surface of the semiconductor substrate. Still further, the electrolyte should be chosen to have a counter ion type and electrolyte concentration (e.g., 0 to 150 mM salt) that maintains a Helmholtz double-layer during electrodeposition of a uniaxially oriented liquid crystal structure on the surface of the semiconductor substrate. High electrolyte concentration will produce too much current and destroy the Helmholtz double-layer during electrochemical deposition processing. In addition, the solvent should be chosen from a range of organic and aqueous solvents and co-solvents to maintain a Helmholtz double-layer during electrodeposition of a uniaxially oriented liquid crystal structure on the surface of the semiconductor substrate. Conducting polymers and molecular recognition headgroups should be soluble in the solvent or co-solvent used. Finally, the temperature should be greater than the freezing point (fp) and less than the boiling point (bp) of the solvent or co-solvent to maintain a Helmholtz double-layer during electrodeposition of a uniaxially oriented liquid crystal structure on the surface of the semiconductor substrate.

Figure 4B:
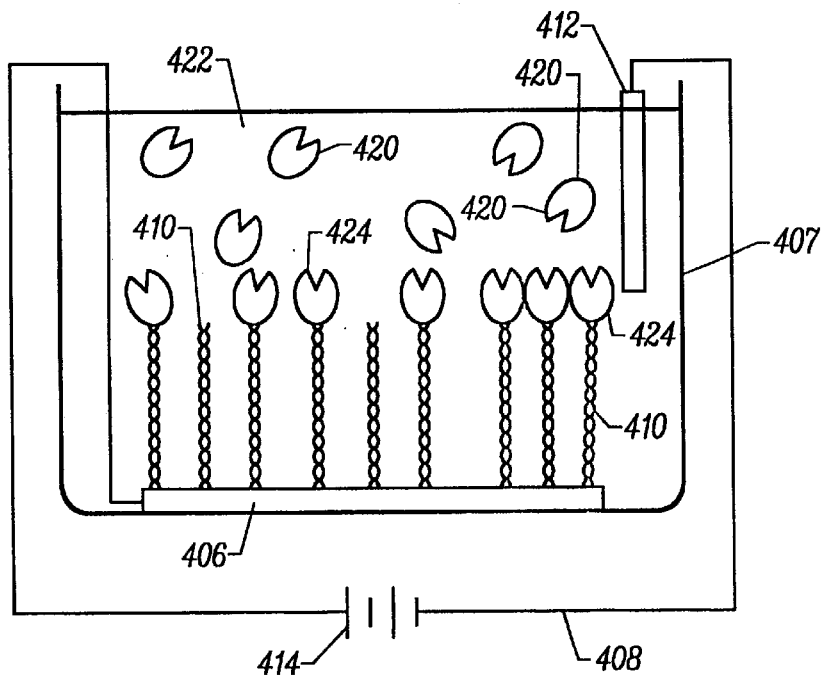
FIG. 4B is representation of an electrodeposition step for attaching molecular recognition headgroups to molecular wires (deposited as shown in FIG. 4A) in accordance with an embodiment of this invention.

During the sensor formation process, a second electrodeposition cycle is performed to attach molecular recognition sites on top of the underlying uniaxially oriented liquid crystal conducting polymer layer. The second cycle is depicted in FIG. 4B. As with the first deposition cycle, a desired material is deposited from a medium; preferably a liquid medium 422. In this case, second medium 422 contains headgroups 420, or an appropriate precursor, to be deposited. After medium 422 is brought into contact with substrate 406 (to which polymer strands 410 were affixed in the first cycle), a potential is applied to the substrate through circuit 408 to drive the second cycle. The potential will be positive or negative depending upon the charge on the headgroups. This results in deposition of a lawn of immobilized headgroups 424 attached to an unfixed end of polymer strands 410. The potential and/or current density should be controlled to ensure that (1) the headgroup is affixed to the polymer strands with strength to allow electron transport, and (2) the deposited headgroups have a substantially common orientation. Deposition cycle variables are adjusted to ensure production of a single molecular layer of uniaxially oriented liquid crystal chemically or biologically active molecular recognition sites 424 individually "wired" to underlying uniaxially oriented liquid crystal electrically conducting polymer layer 410. The headgroups to be deposited may be provided with one, or more functional groups which direct the headgroups onto strands 410 in a desired orientation. As with the polymer strands, the headgroups may be functionalized with a charge group. In many cases, it may be desirable to locate the charge group away from the active site of the headgroup, so that the headgroup will attach with the active site facing the medium.

Deposition conditions must be tailored to the material to be deposited. In one embodiment of this invention, DNA deposition and GOD enzyme deposition conditions happened to use similar current density and applied potential (e.g., 10 to 300 $\mu$A cm$^{-2}$ and 10 to 300 mV). However, solution conditions in the two deposition cycles (i.e., concentration of deposited material, pH, electrolyte, solvent) will not be the same.

As should be apparent, the deposition reactions require that the polymer strands and recognition headgroups be electrically charged and mobile in an electric field. Thus, the compositions of the first and second media may have to be carefully chosen. Typically, though not necessarily, the first medium is removed and the substrate is allowed to dry before being contacted with the second medium.

1. Deposition of Uniaxially Oriented Liquid Crystal Conducting Biopolymers (Proteins and DNA)

In a preferred embodiment of the present invention, EMOLE methods are used to sequentially deposit, attach, and orient liquid crystal conducting polymers (e.g., DNA and proteins) onto the surface of a substrate (e.g., a p-type silicon of a polycrystalline p-n junction solar cell). For example, the pH of a DNA-electrolyte deposition solution is adjusted to ~6.0 (more than two pH units above the $pK_a$ or pI of DNA) producing a negatively charged DNA biopolymer. Light induced photoconduction by a submerged solar cell generates an electric field in the DNA-electrolyte solution which uniaxially orients negatively charged DNA strands onto the positive p-type silicon surface. Solar cell applied current density and voltage potential are low enough to establish and maintain a Helmholtz double-layer (as described in U.S. Pat. No. 5,215,631 to Westfall) between the p-type silicon surface and the DNA and counter ions in solution. The very gentle SMOLE conditions facilitate electrochemical deposition of uniaxially oriented liquid crystalline extended DNA structures orthogonal to the semiconductor substrate surface. By "gentle," it is meant that the conditions preserve the Helmholtz double-layer as described in the Westfall reference discussed above.

EMOLE methods may be used to sequentially deposit, attach, and orient liquid crystal conducting protein (i.e., molecular recognition sites) on top of the underlying uniaxially oriented liquid crystal DNA layer affixed to the surface of the silicon substrate chip. For example, the pH of a protein-electrolyte deposition solution is ~7.0 (more than two pH units above the $pK_a$ or pI of the protein) producing a negatively charged protein biopolymer. Light induced photoconduction by a submerged solar cell generates an electric field in the protein-electrolyte solution which uniaxially orients negatively charged proteins onto the "lawn" of liquid crystal DNA molecular wires. Solar cell applied current density and voltage potential are low enough to establish and maintain a Helmholtz doublelayer between the DNA-modified p-type silicon surface and the protein and counter ions in solution. The very gentle EMOLE conditions facilitate sequential electrochemical depositions that maintain the first monolayer of uniaxially oriented liquid crystalline extended DNA structures orthogonal to the semiconductor substrate surface while depositing a second monolayer of uniaxially oriented liquid crystalline protein "headgroups" on top of the underlying "lawn" of liquid crystal DNA wires as characterized by the following references: Collings, P J: Chap. 3. Electric and Magnetic Field Effects. In: Liquid Crystals: Nature's Delicate Phase of Matter. Princeton University Press; Princeton, N.J.; 1990; pp. 35–55. Collings, P J: Chap. 9. Polymer Liquid Crystals. In: Liquid Crystals: Nature's Delicate Phase of Matter. Princeton University Press; Princeton, N.J.; 1990; pp. 162–180. Pelzl, G: Chap. 2. Thermodynamic Behavior and Physical Properties of Thermotropic Liquid Crystals. In: Liquid Crystals. Stegemeyer, H; guest ed. Steinkopff, Darmstadt and Springer, N.Y.; 1994; pp. 51–102. Zentel, R: Chap. 3. Liquid Crystalline Polymers. In: Liquid Crystals. Stegemeyer, H; guest ed. Steinkopff, Darmstadt and Springer, N.Y.; 1994; pp. 103–141).

Upon electrochemical deposition of a monolayer of uniaxially oriented liquid crystal protein, the DNA-silicon substrate is removed from the deposition bath and allowed to slowly dry and cool in the presence of an applied electric field. This allows the oriented liquid crystal protein structure to be "locked-in" on top of the oriented liquid crystal DNA molecular wire terminal surface of the dry silicon substrate chip as described in the following references: Collings, P J: Chap. 6. Liquid Crystal Displays. In: Liquid Crystals: Nature's Delicate Phase of Matter. Princeton University Press; Princeton, N.J.; 1990; pp. 967–120. Albrecht, C; Enkelmann, V; Lieser, G; Schwiegk, S; Wang, W; Wegner, G; Zierer, D: The Crystallization Behavior of Rod-Like Macromolecules. In: Crystallization of Polymers. Dosiere, M; ed. Kluwer Academic Publishers; Dordrecht, Boston, London; 1993; pp. 323–330. Brandes, R: Part I. Generation of Tailored Radio Frequency Pulses For NMR. Part II. Deuterium NMR Studies of Oriented DNA, and Its Interaction With Water. Dissertation, Ph.D. in Chemistry; University of California, San Diego; 1988.

Because EMOLE employs an electrodeposition mechanism, the species to be deposited must be charged. Such charge exists naturally on many materials of interest when n the solution phase. However, many materials must be charged to facilitate EMOLE deposition. Many biopolymers, for example, can be positively charged by adjusting the pH of the biopolymer-electrolyte deposition solution to more than two pH units below the $pK_a$ or pI of the biopolymer. The resulting positively charged species is suitable for electrochemical deposition onto negative n-type semiconductor surfaces, for example.

Like all liquid crystals, the oriented polymers of this invention may have their properties tailored by adding suitably functionalized groups of atoms to the polymer backbone. Such properties include mechanical strength as well as ferroelectricity, nonlinear optical activity, and electronic charge transfer. The physical principles involved are summarized in a number of books (Collings, P J: Liquid Crystals. Nature's Delicate Phase Of Matter. Princeton University Press; Princeton, N.J.; 1990. Stegemeyer, H (guest ed.): Liquid Crystals. Steinkopff, Darmstadt and Springer, N.Y.; 1994. Plate, NA (ed.): Liquid-Crystal Polymers. Plenum Press; N.Y., London; 1993. Dosiere, M (ed.): Crystallization of Polymers. Kluwer Academic Publishers; Dordrecht, Boston, London; 1993). Anisotropic chemical and physical properties of liquid crystals and liquid crystal polymers are a result of the molecular-scale structure formed. It was recently realized that manipulation of molecular-scale structure, and therefore function of liquid crystals and liquid crystal polymers, not only depended on the use of different functionalized organic molecules, but was heavily dependent on variables such as solvent, electrolytes, impurities, dopants; liquid crystal field effects (i.e., applied electric, magnetic, temperature, mechanical, electromagnetic radiation, or chemical fields); and processing techniques used (Collings, P J: Liquid Crystals. Nature's Delicate Phase Of Matter. Princeton University Press; Princeton, N.J.; 1990. Stegemeyer, H (guest ed.): Liquid Crystals. Steinkopff, Darmstadt and Springer, N.Y.; 1994. Plate, N A (ed.): Liquid-Crystal Polymers. Plenum Press; New York, London 1993. Dosiere, M (ed.); Crystallization of Polymers. Kluwer Academic Publishers; Dordrecht, Boston, London; 1993. Collyer, AA (ed.): Liquid Crystal Polymers: From Structures To Applications. Elsevier Applied Science; London, New York; 1992. Lam, L; Prost, J (eds.): Solutions In Liquid Crystals. Springer-Verlag; New York, Berlin, Heidelberg, London; 1992). For example, coupling of molecular recognition surfaces to electronically conducting polymers may result from chiral smectic (layered cholesteric) liquid crystal structures formed by sequential deposition of DNA and protein using EMOLE fabrication techniques provided by this invention. In a preferred embodiment, biopolymers (DNA and protein) and EMOLE techniques are used to fabricate a molecular recognition (MR) device.

IV. Conducting Polymers and Thin Films

Many different conducting polymers and thin films can be employed for "wiring" molecular recognition sites to a semiconductor or standard electrical component substrate. Generally such polymers may be biological, organic, inorganic, water soluble, lipid soluble or combinations thereof. Many examples of conducting polymers suitable for this invention are discussed by Skotheim, TA: Handbook Of Conducting Polymers. Vol. 1–2. Skotheim, T A, ed. Marcel Dekker, Inc.; New York, Basel; 1986. Types of conducting polymers and thin films suitable for use in this invention include, but are in no way limited to the following general classes: aromatic metal-doped polymers (e.g., polyaniline doped by metal salts), π-stacked (aromatic) polymers (e.g., polyphenanthroline; pyrazine-bridged polymers of π-stacked metalloporphyrins; 2, 3, 6, 7, 10, 11-hexahexylthiotriphenylene (HanT)), π-stacked (aromatic) helical polymers (e.g., DNA), organic π-conjugated linear polymers (e.g., polyacetylene), heterocyclic polymers (e.g. DNA, polyporphyrins), macrocyclic polymers (e.g., polyporphyrins with a redox metal; polytetrazacyclododecane with a redox metal), porphyrin polymers, polymer composites (e.g., layered polymer mixtures), polyelectrolyte polymers, (e.g., proteins, DNA), liquid-crystal polymers (e.g., certain proteins; DNA; polyporphyrins; and 2, 3, 6, 7, 10, 11-hexahexylthiotriphenylene (HHTT), self-organizing polymers (e.g., polysurfactants with redox metal; HHTT), branched polymers, dendritic polymers (e.g., starburst dendrimers with redox metal), chaotic polymers (e.g., poly $(SiO_2)_n$ in glass with redox polymer), biopolymers (e.g., protein, DNA, polyporphyrins), inorganic polymers (e.g. iron (hydrous) oxides), organometallic polymers (e.g., ferrocene polymers), inorganic/organic hybrid polymers (e.g. iron (hydrous) oxide/polybipyridine complex), metallocene polymers (e.g., polyferrocene), inclusion compound polymers (e.g., polyzeolite with redox metal), mixed doped polymers, colloidal/sol-gel doped polymers (e.g., poly $(SiO_2)n$ with redox metal), ionomers (e.g., DNA, certain proteins, and certain polysurfactants), metal cluster doped polymers (e.g., iron (hydrous) oxide/polybipyridine complex), redox polymers (e.g., Heller (Osmium-PVP) and Skothiem (ferrocent-polysiloxane)), block polymers, graft polymers, transition metal films (e.g., deposited by atomic layer epitaxy (ALE)), high temperature superconductor films (e.g., atomic layer epitaxy (ALE) of appropriate redox metals), Langmuir-Blodgett films (e.g., detergents; amphiphiles, surfactants), sol-gel glass films (e.g., spin glass films), etc., or any combinations of the above. Conducting polymers of appropriate strand lengths for each of these may be employed herein.

In some cases, the native form of the polymer will be an insulator, but upon appropriate doping, addition of impurities, hydration, conformational change, ionization, oxidation, reduction, etc. they become conductive. Further, some conducting polymers may be reversibly switched between conductive and insulative states. Polyaniline, for example, will become conductive in the protonated or oxidized form. Other "swichable" conductive polymers include, for example, polymers polymerized from the following monomers: N-methylpyrrole, thiophene, 3-methylthiophene, 3,4-dimethylthiophene, vinylferrocene, styrene, nitrostyrene, viologens, vinyl-pyridine, vinyl-2,2'-bipyridine, vinylrubrene, quinone-based compounds, and derivatives thereof. This invention may also take advantage of such conductivity transformation as a primary or auxiliary sensing mechanism. For example, a sensor signal may only be triggered by a combination of two events: a ligand binding with a molecular recognition headgroup and a pH change which causes the polymer wiring to become conductive.

Enzymes used in organic synthesis (i.e., to produce drugs and pharmaceuticals), may be used as molecular recognition headgroups of this invention. These include, but are not limited to, combinatorial and commercial libraries of esterases, lipases, amidases, acylases, and other thermophilic and mesophilic enzymes with broad substrate specificities that can catalyze reactions in organic solvents and at high temperatures. Upon ligand binding to an esterase or lipase, a reaction will take place producing an alcohol and carboxylic acid from the cleaved ester bond. This will make the pH of the headgroup/switchable polymer molecular environment more acidic; thus, protonating a reversibly switchable polymer to the protonated or conducting form. Amidase or acylase cleavage of an amide bond will produce a free amine and a carboxylic acid. Chelation of the acid by anion exchange support would leave an increasing concentration of free amine which would make the pH of the headgroup/switchable polymer molecular environment more basic; thus, deprotonating the reversibly switchable polymer to the neutral or insulating form. Examples of enzymes used in organic syntheses may be used as molecular recognition headgroups to monitor levels of drugs and pharmaceuticals in the human blood.

Esterase, lipases, acylases, or amidases may also be used to deprotect ligands to alcohols, carboxylic acids, or free amines which then become substrates suitable for a second molecular recognition headgroup, used to produce a signal by methods described in the present invention. For example, cholesterol esterase cleaves cholesterol ester found in blood to cholesterol, which is then a substrate for cholesterol oxidase. Cholesterol oxidase would produce a signal much like glucose oxidase described as an example of this invention.

Other approaches include, for example, Swager, et al. (Swager, T M; Marsella, M J; Conducting Polymers With Chemical Sensitive Traps and Barriers: New Molecule-Based Sensors. Mat. Res. Soc. Symp. Proc. 328:263–266, 1994) which describes reversibly switchable polythiophene derivatives which exhibit large changes in bandgap in the presence of specific ions. These materials are based upon novel crown ethers containing bithiophene monomers. Sensory polymers which are selective for $K^+$ and $Na^+$ are described. In such materials, specific ions induce a twisting of the polymers backbone, resulting in a decrease of π-orbital overlap between thiophene rings; reducing the extent of conjugation giving rise to an insulating (higher bandgap) form.

Another example is of a sequence-specific DNA sensor. A specific sequence of single-strand DNA (nonconducting or insulating form) with 5' or 3' terminus thiol could be adsorbed to a gold electrode substrate. An analyte sample containing the complementary DNA sequence would produce a DNA double-strand polymer which is a conducting form of DNA. This result is a DNA sequence detector. DNA of the wrong sequence would not produce DNA doublestrand polymer (conducting form). Appropriate end group functionalities on single-strand DNA or no end group modifications of single-stranded DNA (i.e., native DNA) using EMOLE methods could be used to put sequence-specific single-strand (insulating form) DNA on semiconductor substrates for use as a DNA sequence detector. DNA at crime scenes could be identified on the spot, doing away with PCR techniques and laborious and very costly DNA sequencing laboratory procedures.

Chemical-, photo-, or electropolymerization of monomers may take place directly on the semiconductor or standard electrical component substrate surface or pre-polymerized polymer, may be deposited. Furthermore, once attached and polymerized, the polymer or thin film may be oriented into a highly conductive liquid crystal polymer or thin film form. This may be accomplished by depositing polymers in the presence of appropriate electrical, magnetic, oir chemical (solvent) fields. Preprocessing or conditioning of polymers is described in the Handbook of Polymer Synthesis (Plastics Engineering Series, Volume 24) Kricheldorf, H. F., 1991. Chemical polymerization may employ, for example, $H_2O_2$, organoperoxides, or 2,2'-azobisisobutyronitrile (AIBN). Photopolymerization may employ photons which generate photochemical radicals which can initiate and propagate polymerzation. Electropolymerization is currently employed to synthesize conducting polymers.

A. Electron Transport Proteins

An example of a conducting biopolymer that may be useful for this invention is the electron transport protein. Electron transport proteins are a product of millions of years of biological evolution, fine tuning the function of electronic conduction. In nature, electron transport proteins often reside in, and are oriented by, a liquid crystalline lipid bilayer membrane. In this invention, the electron transport protein may be deposited into a close-packed oriented two-dimensional crystalline structure by EMOLF crystallization processing techniques. This produces a surface structure suitably oriented as a plurality of molecular wire interconnects.

Proper deposition and orientation of proteins can be accomplished by manipulation of the physical and chemical conditions during crystallization. The EMOLE technique allows a systematic approach understanding and optimizing the relevant parameters for depositing protein or peptide polymers as wires for sensors. More generally, the newly developed techniques of EMOLE provide for experimental control of protein crystal structure and function.

Electron transport proteins are in some embodiments suitable for use with this invention because they perform some of the function desired for molecular electronic device (MED) fabrication—i.e., electron storage and transfer at the molecular-scale. These properties arise from the alpha-helical and beta-pleated sheet structures of these biological macromolecules and from their non-protein prosthetic groups. These prosthetic groups are inorganic-, organometallic-, or metal atom cofactors which are integral to the structure of protein. A particularly interesting protein is cytochrome $b_{562}$ of E. coli. This protein is small (12,000 daltons), has a single polypeptide chain folded into a simple 4-alpha-helical motif, the x-ray structure is known to 2.5 Å, and most importantly, the single heme group is non-covalently bound. This last property allows for the substitution of other porphyrin analogs with a variety of coordinated metal atoms, greatly increasing the experimental flexibility of the system (Ulmeir, K M: Chap. 29. Self-Organizing Protein Monolayers As Substrates For Molecular Device Fabrication. In: Molecular Electronic Devices II. Carter, F L; ed. Marcel Dekker, Inc.; New York, Basel; 1987; pp. 573–590).

Photosynthetic electron transport proteins electronically connecting photosystem II and photosystem I in plants, and mitochondrial respiratory electron transport proteins are examples of conducting biopolymer proteins oriented by a liquid crystalline lipid bilayer membrane—the chloroplast membrane (Clayton, R K: Light and Living Matter, Volume 2: The Biological Part. McGraw-Hill Book Company, New York, 1971) and mitochondrial membrane;, facilitating an extremely efficient electron transfer chain via electron tunneling mechanism (Pethig, R: Chap. 9. Electronic Properties of Biomacromolecules. In: Dielectric and Electronic Properties of Biological Materials. John Wiley & Sons; Chichester, New York; 1979; pp. 290–356).

Electron transport proteins that may be found among the proteins participating in the respiratory chain of mitochondria are for example: flavoproteins, nonheme iron proteins, and cytochromes b, $c_1$, c, a, and $a_3$. With the exception of the electron donor, NADH, all of these are electron transport proteins, shuttling two electrons from each molecule of NADH to reduce ½ $O_2$ to $H_2O$. This downstream free energy electron transport to $O_2$ is coupled to phosphorylative production of ATP, a biochemical energy currency.

Electron transport from photosystem II to photosystem I in the chloroplast membrane of green plants involves the electron transport proteins cytochrome $b_{559}$ or $b_3$ and cytochrome f. Electron transport from photosystem I involves the electron transport proteins ferredoxin and cytochrome $b_6$.

All of these electron transport proteins are juxtaposed to each other in membranes with increasing standard oxidation-reduction potentials facilitating a downward free energy transfer of two electrons from one electron transporting protein to the next in a highly ordered chain.

B. DNA Quantum Wires

A second example of a conducting biopolymer not normally thought of is electrically conductive until recently is DNA (Meade, T J and Kayyem, J F: Electron Transfer Through DNA: Site-Specific Modification of Duplex DNA with Ruthenium Donors and Acceptors. Angew. Chem. Int. Ed. Engl. 34(3):352–354, 1995. Murphy, C J; Arkin, M R; Jenkins, Y; Ghatlia, N D; Bossmann, S H; Turro, N J; Barton, J K: Long-Range Photoinucod Electron Transfer Through a DNA Helix. Science 262:1025–1029, 1993. Meade, T J: Chap. 13. Electron Transfer Reactions Through the DNA Double Helix. In: Metal Ions In Biological Systems. Vol. 32. Interactions of Metal Ions With Nucleotides, Nucleic Acids, and Their Constituents. Sigel, A; Sigel, H; eds. Marcel Dekker, Inc.; New York, Basel, Hong Kong; 1996; pp. 453–478. Stemp, EDA; Barton, J K: Chap. 11. Electron Transfer Between Metal Complexes Bound To DNA: Is DNA A Wire? In: Metal Ions In Biological Systems. Vol. 33. Probing of Nucleic Acids by Metal Ion Complexes of Small Molecules. Sigel, A; Sigel, H; eds. Marcel Dekker, Inc.; New York, Basel, Hong Kong; 1996; pp. 325–365. Arkin, M R; Stemp, EDA; Holmlin, R E; Barton, J K; Hormann, A; Olson, E J C; Barbara, P F: Rates of DNA-Mediated Electron Transfer Between Metallointercalators. Science 273:475–480, 1996). DNA is a biopolymer with known solution and solid-crystal structures. In this invention, deposition of an oriented extended liquid crystalline DNA structure orthogonal to a solid-substrate surface may be achieved by EMOLE crystallization processing techniques. This produces a surface structure suitably oriented as a plurality of molecular wire interconnects.

While not wishing to be bound by theory, the following discussion is presented to illustrate the state of the art as to DNA as a conducting medium. There is still no consensus in the art as to whether DNA can actually act as a wire. The debate is set forth generally by Wilson (Wilson, DNA: Insulator or Wire, Chem. & Eng. News, 1997:33, Feb. 24, 1997) While such debate rages, the following discussion assumes that DNA is in fact a very good conducting polymer and is a preferred wire for use with the sensors and EMOLE methods of this invention.

Long distance electron movement through DNA (i.e., ~40 Å or ~12 base pairs) has been confirmed only in experiments in a water solution. DNA has to be fixed to a terminal base, substrate, etc., coupled with the controlling of the thickness and orientation of molecules in order to measure the accurate conductivity of the fixed DNA. Recently, studies on fixation of DNA to solid bases have been reported by various methods such as ion connection, covalent bond, and protein bonding for the use of DNA as a potential electronic material.

Okahata, et al. prepared a polyion complex using DNA and cation lipids in order to prepare thin cast film membranes of DNA (Ijiro, K and Okahata, Y: A DNA-Lipid Complex Soluble in Organic Solvents. J. Chem. Soc., Chem. Commun. 1992:1339, 1992). Phosphate and cation lipids formed quantum chemical ion pairs. As a result, an alkyl base covered the DNA forming the shape of a brush to wash a test tube and became hydrophobic and settles instantly. Nishi et al. prepared the gel film with the thickness of 2–3 $\mu m \times 2$–3 mm by adding bivalent metallic ions such as $Ca^{2+}$ or $Mg^{2+}$ to a water solution of alginic acid, a polysaccharide having a residue of alginic acid (Iwata, K; Nishi, N; Miura, Y; Nishimura, S; Tokura, S: Polymer Preprints, 42:599, 1993). DNA structure was maintained in the film from adsorbtion test of intercalator color in the study. The molecular orientation of DNA in the film prepared by fixation methods was random and was very difficult to control the molecular orientation and thickness of the membrane. G. Decher et al. reported on the methods for preparing the thin membrane of DNA which had a thickness of one molecule (Lvov, Y; Decher, G; Sukhorukov, G: Assembly of Thin Films by Means of Successive Deposition of Alternate Layers of DNA and Poly(Allylamine). Macromolecules 26:5396–5399, 1993). High molecular weight DNA isolated from sturgeon sperm formed layers 33 Å thick by x-ray diffraction indicating the DNA spread two-dimensionally with the long axis parallel to the substrate surface. In conventional studies, fixation was performed using the ion connection of anion phosphates at multiple points. On the other hand, Maeda et al. reported the fixation methods fixed the special edge of DNA on a gold terminal by chemically treating the edge of DNA with a thiol base (Maeda, M; Nakano, K; Uchida, S; Takagi, M: $M^{2+}$-Selective Electrode Comprising Double-Helical DNA as Receptive Entity. Chem. Lett. 1994:1805–1808, 1994). Organic thiol compounds bind strongly to gold. Maeda et al. considered that the orientation of DNA was vertical towards the terminal from the measurement of the amount of fixed DNA. Ijiro et al. reported a production of a semi-molecular membrane using DNA, a cation intercalator lipid ($C_{18}$-acridine orange), and Langmuir-Blodgett techniques of casting a thin film. Orientation of the DNA strings was attempted by applying compression and measuring conductivities in different directions (Ijiro, K; Shimomura, M; Tanaka, M; Nakamura, H; Hasebe, K: Thin Solid Films (in press). Ijiro, K and Shimomura, M: Double-Stranded DNA for Molecular Electronic Devices. Kotai Butsuri 30(12):1042–1048, 1995. Birdi, K S: Lipid and Biopolymer Monolayers at Liquid Interfaces. Plenum Press; New York, London; 1989). As evidenced by this review of various methods for fixation of DNA on surfaces, there is some difficulty in orienting DNA films for use as routine commercial electronic materials providing high density molecular wire interconnects on common semiconductor or standard electrical component substrates.

In a preferred embodiment of this invention, DNA or nucleic acid is used as the conducting polymer precursor to be electrochemically deposited and uniaxially oriented into a highly conductive liquid crystalline form on the semiconductor substrate surface. Single-stranded DNA is not electrically conductive as a molecular wire. It is a random coil with little order. However, double-stranded A-, B-, or Z-DNA are examples of flat heteroaromatic purine and pyrimidine $\pi$-stacked base pairs (i.e., heteroaromatic $\pi$-stacking of flat base pairs, one on top of the next in a rising helix) that makes double-stranded DNA conductive. Other examples of suitable DNA structures that may be deposited as uniaxially oriented liquid crystalline DNA quantum wires include, but are in no way limited to clockwise double-stranded twining structures, otherwise called A-, B-, C-, D-, E-, and T-types. DNA also has a counterclockwise double-stranded twining structure, called Z-type. In addition, there is looped DNA which consists of thousands of pairs of bases called plasmid DNA which exists in prokaryotic organisms. There is also a twisted looped DNA structure which comprises several loops and a super helical structure. There even exists a twisted loop, cross shaped DNA (Ijiro, K and Shimomura, M: Double-Stranded DNA for Molecular Electronic Devices. Kotai Butsuri 30(12):1042–1048, 1995). And DNA exists in triple helix type structures as well (Povsic, T J; Dervan, P B: Triple Helix Formation By Oligonucleotides On DNA Extended To The Physiological pH Range. J. Am. Chem. Soc. 111(8):3059–3061, 1989).

Preferably, a liquid crystal B-DNA tpe double-stranded structure is deposited, electrically attached, and uniaxially oriented in parallel extended conformation orthogonal to the surface of a semiconductor in specific chemically or electrochemically activated regions (as shown in FIG. 2). A and T; G and C complementary pairs of bases form an upright Duplex helical structure with a diameter of approximately 20 Å, comprising two high molecular chains. The pitch of the duplex helical structure is approximately 34 Å and 10 of the pairs of bases line up vertically towards the extended line of DNA. The upper and lower pairs of bases create an angle of 36° while the distance between each pair of bases is 3.4 Å. This produces a strong mutual relationship between each stuck pair of bases inside the duplex helical structure of DNA. For example, an extreme reduction of absorbance (light color effect) will occur because of $\pi$—$\pi^*$ conversion. In other words, the internal characteristics of DNA can be considered as a suspected one-dimensional crystalline structure of stuck pairs of bases (Ijiro, K and Shimomura, M: Double-Stranded DNA for Molecular Electronic Devices. Kotai Butsuri 30(12): 1042–1048, 1995).

Particularly high packing efficiencies are achieved in the icosahedral double-stranded DNA bacteriophages, where the DNA duplexes are close packed at a center-to-center spacing of about ~26 Å. This constraint has been incorporated into several recent models in all of which the rods of duplex DNA are configured in more-or-less parallel bundles (Booy, F P; Newcomb, W W; Trus, B L; Brown, J C; Baker, T S; Steven, A C: Liquid-Crystalline, Phage-Like Packing Of Encapsidated DNA In Herpes Simplex Virus. Cell 64:1007–1015, 1991). Moreover, the average 26 Å interduplex spacing closely resembles that observed for liquid crystals of DNA in vitro by cryoelectron microscopy or x-ray diffraction (Booy, F P; Newcomb, W W; Trus, B L; Brown, J C; Baker, T S; Steven, A C: Liquid-Crystalline, Phage-Like Packing Of Encapsidated DNA In Herpes Simplex Virus. Cell 64:1007–1015, 1991). In a preferred embodiment of this invention, uniaxially oriented liquid crystalline B-DNA conductive wires are electrochemically deposited at specific light activated regions on the surface of a p-n junction solar cell by EMOLE fabrication methods as described above.

V. Molecular Recognition Surfaces

A molecular recognition surface preferably is made up of a two-dimensional crystal array of one or more molecular recognition site(s) that recognize a particular ligand (i.e., analyte) typically, though not necessarily, in a liquid. In addition to its ability to bind specific ligands, a molecular recognition site may also be a catalytic site, redox site, electron transfer site, energy transfer site, magnetic transfer site, and as a consequence of ligand binding may induce conformational change, and quantum-confined electron/hole tunneling and percolation.

The molecular headgroups employed in this invention include, for example, proteins (which bind ligands), catalytic antibodies, porphyrin, lectins, enzymes (including any enzyme categorized in the EC Nomenclature—e.g., class 1: oxidoreductases, class 2: transferases, class 3: hydrolases, class 4: lyases, class 5: isomerases, and class 6: ligases), immunological antibodies antigens, receptors, viruses, cells, cavitands, zeolites (which bind redox metals), supramolecular assemblies, electro-optical materials (e.g., second- and third-order nonlinear optical materials), photoconductive and photoelectric materials (in which an applied electromagnetic field produces free electrons), giant magnetoresistive materials (in which an applied magnetic field changes resistivity of the material), metal chelates, magnetic materials (in which magnetic ordering is changed by the presence of other magnetic materials), inorganic scintillators (which convert high energy radiation to lower energy light photons), inorganic crystal oscillators (which act as a quantum frequency transmitter and receiver), piezoelectric materials (in which mechanical force produces electron flow), light-harvesting polymer systems (in which light produces electron flow and chemical energy storage), laser switch dyes (which absorb light at one wavelength and emit a monochromatic light at a longer wavelength), barrier tunnel switches (e.g., molecular electron switches), etc.

Examples of ligands that can be used with this invention include, but are not restricted to, agonists and antagonists for cell membrane receptors, toxins and venoms, viral epitopes, antigenic determinants, monoclonal and polyclonal antibodies, hormones, hormone receptors, steroids, peptides, enzymes, substrates, cofactors, drugs, lectins, sugars, oligonucleotides, oligosaccharides, proteins, transition metals, chelates, cavitands, pollutants, chemical and biological warfare agents, poisons, dyes, gases, intercalators, alcohols, alkaloids, fats, lipids, cholesterol, blood type, cell surfaces, metabolites, etc.

Molecular recognition sites that mediate a biological or chemical function either directly or indirectly on binding with a particular ligand(s) are of most interest. Suitable molecular recognition sites include relatively small, single molecules, such as cofactors, which show specific binding properties. Typically, molecular recognition sites will range from 1 dalton lo greater in size. Other examples of molecular recognition sites include, but are not restricted to, the common class of receptors associated with the surface membrane of cells and include, for instance, the immunologically important receptors of B-cells, T-cells, macrophages and the like. Other examples of molecular recognition sites that can be investigated by this invention include but are not restricted to hormone receptors, hormones, drugs, cellular receptors, membrane transport proteins, electron transport proteins, steroids, peptides, enzymes, substrates, cofactors, vitamins, lectins, sugars, oligonucleotides, intercalators, oligosaccharides, viral epitopes, antigenic determinants, glycoproteins, glycolypoproteins, immunoglobins, restriction enzymes, catalytic antibodies, transition metals, chelates, cryptands, cavitands, supramolecular structures, etc.

A. Oxidoreductases (Redox Enzymes)

Examples of molecular recognition sites that bind specific ligands, catalyze a redox reaction, and are electrically conducting biopolymers, are a broad class of enzymes called the oxidoreductases. To this class belong all enzymes catalyzing oxido-reductiong. The substrate oxidized is regarded as hydrogen or electron donor. The classification is based on 'donor:acceptor oxidoreductase'. The recommended name is 'dehydrogenase', wherever this is possible; as an alternative, 'acceptor reductase' can be used. 'Oxidase' is only used in cases where $O_2$ is an acceptor. Classification is difficult in some cases because of the lack of specificity towards the acceptor. The EC number 1.x.x.x as it appears in Enzyme Nomenclature (1978) is,; assigned to the class called oxidoroductases (Enzyme Nomenclature. Academic Press; New York; 1978).

Oxidoreductases or redox enzymes are molecules of 40,000 daltons (e.g., galactose oxidase) to 850,000 daltons (e.g., choline dehydrogenase) with one or more redox centers. Their average hydrodynamic diameters range from ~55 to ~150 Å. In the great majority of enzymes, the redox centers are located sufficiently far from the outermost surface (defined by protruding protein or glycoprotein domains) to be electrically inaccessible. Consequently, most a enzymes do not exchange electrons with electrodes on which they are adsorbed, i.e., their redox centers are neither electrooxidized at positive potentials nor electroreduced at negative ones. Apparently, part of the protein or glycoprotein shell surrounding the redox centers is there to prevent indiscriminate electron exchange between the different redox macromolecules of livinlg systems. Another function of this shell is to stabilize the structure of the enzyme. Because neither function is essential for catalysis, redox enzymes do function when part of the shell is stripped or, when the shell is chemically altered so as to make it electrically conductive.

Examples of oxidoreductase enzymes suitable for use with this invention include glucose oxidase, catalase, peroxidase, cholesterol oxidase, and alcohol dehydrogenase. Glucose oxidase (GOD) turns over at ambient temperature at a rate of ~$10^2$ s$^{-1}$, i.e., it produces about 200 transferable electrons/s. Because it has a radius of ~43 Å, there can be up to $1.7 \times 10^{12}$ enzyme molecules on the electrode surface. The current density, when all redox centers are electrically well connected to the electrode, may thus reach about $3.4 \times 10^{14}$ electrons s$^{-1}$ cm$^{-2}$, or 53 $\mu$A cm$^{-2}$.

In a preferred embodiment, molecular recognition site(s) will be composed of one or more of the following oxidoreductases (redox enzymes): glucose oxidase (GOD) which binds specifically to D-glucose, cholesterol esterase/cholesterol oxidase (COD) which binds specifically to cholesterol ester/cholesterol, catalase (CAT) which binds specifically to $H_2O_2$, or alcohol dehydrogenase (ADH) which binds specifically to ethanol. All of these redox enzymes oxidize their respective substrates, transferring two electrons to natural or artificial diffusible electron acceptor mediators. In the present invention, a uniaxially oriented liquid crystal conducting biopolymer in an extended straight conformafion is stuck or "wired" into each catalytic site/redox center permitting direct electron transfer to take place. Electron transfer to natural diffusible electron acceptors such as $O_2$ or other artificial diffusible redox mediators such as ferrocene or metal derivatives is therefore largely eliminated. Mechanism of electron transfer in the present invention is based on a solid-state "hard-wired" organization at the enzyme catalytic site/redox center establishing quantum-confined electron/hole tunneling and percolation through a uniaxially oriented liquid crystal conducting polymer or biopolymer known as a molecular or quantum wire. Electron or hole injection from a molecular recognition headgroup (i.e., oxidoreductase) through an attached superconducting quantum wire tail (i.e., DNA) interconnect to an underlying electronic substrate is the basis of a molecular transistor.

In a preferred embodiment of this invention, a plurality of such molecular recognition sites (i.e., enzymes) are electrochemically deposited onto the surface of a p-n junction solar cell by first depositing liquid crystalline highly oriented B-DNA "molecular wires" to the p-type surface. Preferably, a liquid crystalline molecular recognition surface structure is deposited, electrically attached, and uniaxially oriented at the surface of a liquid crystal B-DNA double-stranded structure which was deposited, electrically attached, and uniaxially oriented at the surface of p-type semiconductor in specific chemically or electrochemically activated regions. Oriented DNA duplex polyelectrolytes likely are extended, straight quantum wires that penetrate deeply into enzyme crevices at one end and semiconductor substrate at the other end. This type of molecular-scale structure likely facilitates direct, quantum mechanical electron transfer between enzyme headgroups and semiconductor substrate.

In a preferred embodiment, spatially addressable electrochemical activation at specific regions on the surface of a p-n junction solar cell is achieved by light masking or photolithographic techniques for the purpose of electrodeposition at specified locations on the chip. In a preferred embodiment of this invention, liquid crystalline highly oriented molecular recognition surfaces are electrochemically deposited at specific light activated regions on the. surface of a p-n junction solar cell by EMOLE methods as described above. Preferably, DNA wires on the p-n junction solar cell are exposed to light at specific regions to form electrical contacts with liquid crystal oriented molecular recognition sites by EMOLE methods. This is repeated at different regions on the semiconductor surface to pattern complex digital organic integrated circuits (IC) of "wired" molecular recognition sites. The fabrication scheme described above constitutes preferable production methods of a molecular recognition chip (MRC).

B. Immunoglobulins

If we are looking for a more general method of incorporating non-biological molecules into molecularly organized materials, then the immunoglobulins or antibody molecules offer many attractive advantages. Using currently available monoclonal antibody technology, it is now possible to generate a specific immunoglobulin molecule capable of binding to almost any compound of interest. In accordance with the present invention, one could engineer crystals of antibody complexes in which it was possible to control the arrangement and orientation of the complexed molecules at the molecular-scale. There has already been a report of successful application of Langmuir-Blodgett techniques to produce two-dimensional crystals of antibody molecules which may be used for MED development.

Examples of molecular recognition sites that bind specific ligands, catalyze it redox reactions, undergo conformational change and are electficnlly conducting biopolymers, are, aa broad class of proteins called immunoglobulins. Catalytic antibodies are man-made immunoglobulins that can be engineered to possess all of the above chemical and physical properties and specificity for a particular ligand. In a preferred embodiment, immunoglobulins or catalytic antibodies may be deposited as molecular recognimon headgroups onto DNA quantult wires using EMOLE crystallization processing techniques as described above to fabricate molecular recognition (MR) devices on a macro-solid substrate.

VI. Conduction Mechanisms through Polymers on Solid Substrates

A. Energy Bands in Uniaxially Oriented Liquid Crystal Conducting Biopolymers (Proteins and DNA) and Semiconductor Substrates Since Szent-Gyorgyi's report that biopolymers can work like semiconductor, many researchers have pursued research on electron movement through proteins. The potential for long-range electron movement within a protein coupled with double helix DNA was theoretically calculated from the point of quantum chemistry. Because ionic impurities are present in DNA, the methods used to prepare solid pellets varied depending on the experiments and thus, reported conductivities have varied between $10^{-4}$ and $10^{-10}$ mho $m^{-1}$. A quantum mechanical-based model also offers a possible explanation for the anomalously rapid long-range (i.e., ~40 Å) photoelectron transfer recently observed by Barton and Turro et al. for donor and acceptor species intercalated into a DNA double helix.

There is no possibility of intrinsic conductivity in periodic and aperiodic polypeptide chains due to their large fundamental energy gap. This conclusion may appear, at first glance, to be a stumbling block to the electronic conduction in proteins. It should however be noted that many other materials, the glasses, oxides and amorphous semiconductors, also have energy gaps sufficiently large to make them poor conductors but this has not prevented consideration of them in electronic terms and the establishment of a considerable body of experimental and theoretical evidence for long range electron transfer in them.

Since the bands in the density of states (DOS) curves of aperiodic chains are very broad with a few small gaps, there is a possibility of extrinsic conduction on doping with electron acceptors (p-doping) or with electron donors (n-doping) in these chains. To decide about the nature of extrinsic conduction (whether Bloch-type conduction or charge transport through hopping) one needs to investigate the localization properties of the wavefunctions belonging to the energy levels in the upper part of the valence band region or the lower part of the conduction band region (these are the regions of interest if a charge transfer is to take place in vivo due to the interaction of proteins with electron acceptors or donors or with DNA). The possibility of this type of charge transfer has also been suggested by Szent-Gyorgyi.

Quantum mechanical models proposed to estimate energy bands and electronic conduction in proteins and DNA can be influenced by a numbers of external factors which tend to reduce or eliminate the bandgap and broaden the width of estimated valence and conduction bands. This yields biopolymers with metallic-like conduction properties. Such external factors include impurities, dopants, applied electric fields, applied magnetic fields, illumination (hv), hydration with $H_2O$, solvent, pressure, conformational changes, orientation, pH, electrolytes, local surface charges, and injection of electron or holes directly into the conduction or valence bands of the biopolymer. Injection of electrons into protein conduction bands can come from $COO^-$ groups on protein side chains or at the carboxyl terminus, and from $H_2O$. Selective application of these external factors effects are used to engineer bandgap structure of proteins and DNA using EMOLE fabrication techniques to produce desired physical and chemical properties of superconducting, conducting, semiconducting, or insulative forms. EMOLE provides energy band matching and molecular interconnects between proteins, DNA, and the semiconductor substrate which affords quantum mechanical electronic conduction.

Uniaxially oriented liquid crystalline forms of conducting biopolymers (proteins, and DNA) may be produced by EMOLE fabrication techniques. Processing variables utilized by EMOLE to deposit oriented liquid crystal conducting biopolymers include external factors influencing biopolymer energy band structures described above. EMOLE is a chip fabrication method used to engineer molecular structure, energy band structure, band matching, and quantum mechanical molecular interconnects of conducting biopolymers (proteins and DNA) on the surface of a semiconductor substrate.

In order for communication between uniaxially oriented liquid crystal conducting biopolymers (proteins and DNA) and the polycrystalline or monocrystalline macro-semiconductor substrate of the MR-device, common energy levels must exist between not only, the protein (molecular headgroup) and DNA (quantum wire tail) components, but between the DNA and the semiconductor substrate. In MR-devices of the present invention, DNA duplex polyelectrolytes are extended, straight quantum wires that penetrate deeply into enzyme crevices at one end, and into the macro-semiconductor substrate at the other end. This type of molecular-scale structure facilitates direct electron transfer from the enzyme prosthetic group and desired energy continua between enzyme, DNA, and semiconductor substrate. The nature of the energy continua is similar to the ideas proposed by Szent-Gyorgyi in 1946, Pethig, Bathaski, Tanatai; and others regarding a common quantum mechanical energy band continuum, resonant tunneling, hopping, acoustic plasmon, etc. mechanisms which facilitate charge transfer of mobile charge carriers (electrons or holes) through protein and DNA to the underlying semiconductor substrate.

B. Superconductivity

The possibility that superconductive phenomena may play a biological role is at present a controversial subject in several laboratories. Unlike the situation for normal electronic conductors, electrons in a superconductor are not free to move independently of each other but exist as coupled electron pairs constrained to be in the same quantum state. As a result of this pairing-up of electrons, electron scattering effects are minimized with the result that the flow of electron current can occur without the generation of heat and hence with no electrical resistance. Such an effect could obviously have far-reaching consequences if it could be detected in biological systems at physiological temperatures. In conventional superconductors the electron pairing results from interactions between the electrons and the lattice phonons. In 1964, Little proposed that suitably constructed organic polymeric systems would be capable of sustaining superconductivity as a result of an electron-pairing mechanism involving electron-exciton interactions (Little, WA: Possibility of Synthesizing an Organic Superconductor. Phys. Rev. 134(6A):A1416–A1424, 1964.). Little estimated that such a polymer, consisting of a conducting conjugated hydrocarbon backbone and side chains in the form of highly polarizable dye molecules, would be superconducting up to temperatures of the order 2200° K. Such high. temperatures would obviously not be realistic for organic systems for reasons of thermal stability, but this estimate of the critical temperature does serve to indicate that the concept of the existence of superconducting biopolymers at physiological temperatures lies well within the limit of the applicability of Little's theory. The existence of superconductivity in aromatic compounds; was first speculated upon by London (London, F J: J. Phys. Radium 8:397, 1937); and Ladik et al. (Ladik, J; Biczo, G; Redly, J: Possibility of Superconductive-Type Enhanced Conductivity in DNA at Room Temperature. Phys. Rev. 188(2):710–715, 1969) have provided a theoretical basis for the superconductive behavior of DNA.

Experimental evidence for high temperature superconduction in biological molecules has been reported in several laboratories. Superconductivity was deduced to occur in small domains included in the insulating bulk of bile cholate test samples and so as to distinguish the effects from that normally found for the elemental superconductors, the cholates were designated a fractional or Type m superconductor. When small amounts of water are introduced into such materials the hydrophobic groups will tend to cluster together, and on subsequent slow desiccation small micelles will be formed. Such micelles are considered by Halpern and Wolf to form superconducting domains.

Following the suggestion that enzymes and other biological materials possess a metastable state with high dipole moment, Ahmed et al. investigated the dielectric and magnetic susceptibility properties of the dilute solutions of lysozyme (Ahmed, N A G; Calderwood, J H; Frohlich, H; Smith, C W: Evidence For Collective Magnetic Effects In An Enzyme: Likelihood Of Room Temperature Superconductive Regions. Phys. Lett. 53A(2):129–130, 1975). It was found that magnetic fields of the order of 0.6 tesla could produce very large changes (~30%) in the relative permittivity of the solutions. This was suggestive of superconductive behavior. It was suggested that in each lysozyme molecule there existed a small superconductive region with linear dimensions smaller than the London penetration depth, and that the collective, superconductor-like, phenomena resulted from the formation of clusters of these small regions. This is similar to the cluster model proposed for bile cholates. It was also suggested that not only the lysozyme molecules, but also water and ions may have played a role in the establishment of the superconducting regions.

Other indirect evidence to suggest a biological role for superconductivity has been suggested by Cope (Cope, F W: Physiol. Chem. Phys. 3:403, 1971. Cope, F W: Physiol. Chem. Phys. 5:173, 1973) that high temperature superconduction may be expected in a sandwich consisting of a thin conductive film or filament adjacent to a dielectric layer. Cope considers that such superconducting sandwiches may be ubiquitous in biological systems in the form of thin layers of protein and unsaturated lipids and hydrocarbon ring structures (conducting layer) adjacent to layers of water (polarizable dielectric layer). Examples of such biological processes are impulse conduction velocity in frog sciatic nerves and junctional electrical resistance of crayfish nerve. Such an effect can be well described in terms of a model where the rate-limited biological process involves a superconducting tunneling current of single electrons and/or electron pairs (the Josephson current). It was suggested that as there was an apparent association of superconduction with growth, then the superconductive micro-regions may have been individual purine and pyrimidine rings of DNA and RNA with electron tunneling between rings along the length of the polymer chain. It was further suggested that superconductive Josephson junctions in living systems may provide a physical mechanism with more than enough sensitivity to explain how many biological organisms are able to respond to weak magnetic fields.

Two-component plasmas (or more generally multi-component plasmas) as in an electron-hole liquid can support, other than the usual plasmon mode, a new collective mode called the "acoustic-plasmon mode". Quantum mechanical treatment of acoustic plasmons in one dimensional systems such as a long DNA molecule have attracted attention. Tanatar (Tanatar, B: Collective Modes in a Quasi-One Dimensional, Two-Component Electron Liquid. Solid State Communications 92(8):699–702, 1994) stated that a motivation to study the acoustic plasmons in quasi-one-dimensional electron-hole systems comes from the fact that they may provide a pairing mechanism like the BCS theory which leads to a superconducting transition (Bardeen, J; Cooooper, L N; Schrieffer, J R: Microscopic Theory of Superconductivity. Phys. Rev. 106:162–164, 1957). Such an acoustic plasmon mediated superconductivity has been proposed and elaborated for two-dimensional electron-hole liquids. Possibility of superconductivity due to ordinary plasmons in quantum wires were also considered. Experiments to observe the acoustic plasmons in quasi-one-dimensional structures such as DNA, and their possible pairing mechanism leading to superconductivity would be most interesting.

In a preferred embodiment, uniaxially oriented liquid crystal conducting biopolymers (protein and DNA) deposited by controlled EMOLE fabrication techniques are used to produce a functional device. Such devices are thought to function via one or more superconducting mechanism(s) described above. For example, a GOD-DNA device generates an electron pair for each D-(+)-glucose molecule oxidized by the GOD protein enzyme headgroup. Electron pair movement from protein $FAD/FADH_2$ prosthetic group (redox center) through DNA quantum wire to underlying semiconductor substrate occurs via superconducting mechanism(s) described above. Many gated devices inject an electron pair, via superconducting mechanism, into p-type silicon of a p-n homojunction solar cell; combining with photogenerated majority carriers (holes), to lower the baseline photocurrent ($I_{SC}$). Decrease in photocurrent is directly proportional to D-(+)-glucose concentration. Change in photocurrent occurs very rapidly and is accompanied by a near step change (see FIGS. 5 and 6 described below), resulting from differential device injection of mobile charge carriers (electrons or holes) into p-type or n-type semiconductor substrate surfaces.

VII. Applications

The sensors of this invention may be employed for a myriad of applications. For example, sensor based home health monitors will be simple-to-use, non-invasive and relatively inexpensive for use in monitoring health conditions at home. Many physical functions—liver functions, ovulation, pregnancy, yeast infections, viral infections, bacterial infections, levels of cholesterol, triglycerides, sugar, hormones, drugs, water, salt, pH, sodium, and potassium—may be monitored as easily as weight is now tracked by bathroom scales. The graying of our population and the increasing costs of medical care will make these products extremely popular.

In another preferred embodiment of this invention, a sensor, in a portable pen-based device, may be used to monitor compounds found in the human breath. The normal human breath contains hundreds of volatile organic compounds that are reflective of the metabolic state of the person. These volatile organic compounds have been quantitated by gas chromatographic (GC) and mass spectrometry (MS) methods in numerous studies. Preferably, a sensor of this invention is exposed to exhaled breath. In a preferred embodiment, the molecular recognition surface of the sensor will be alcohol dehydrogenase (ADH) which specifically binds to ethanol; reduced mercaptoethanol, glutathione, or dithiothreitol which specifically binds to sulfur containing compounds; or a variety of other molecular recognition sites to detect breath idcompounds readily recognized by those of skill in the art. The ADH-sensor will provide police and highway patrol officers with a portable pen-based breathalyzer to validate drunk driving, violations in the field. The Thio-sensor will provide individuals with a portable pen-based breathalyzer for discrete detection of halitosis (i.e., bad breath).

In another preferred embodiment, a device-based molecular recognition chip (MRC) may be embedded in a magnetoosmotic (MOP) or electroosmotic patch (EOP) which may be applied to the skin for real-time non-invasive quantitation of analytes found below the skin (i.e., analytes in blood and deep anatomic structures). This is a non-invasive approach to analyte quantitation alternate to exposure of the powered chip to invasively drawn blood or other fluids described above. The MRC-MOP or MRC-EOP is suitable for non-invasive detection of small charged, uncharged, and zwitter ionic molecules and salts (i.e., analytes) less than 30,000 daltons found on the other side of complex synthetic or biological barriers such as skin, adipose tissue, vascular walls (i.e., venous and arterial vessel walls), isoparenteral walls, extravascular walls, extracellular walls, cerebral vascular walls, blood brain barrier (BBB), and a variet of other man-made and natural membranes. The MOP, applies a combination of localized magnetic field gradients and hypertonic junctions to surfaces such as skin that it contacts. The EOP, applies a combination of localized electric field gradients and hypertonic junctions to surfaces such as skin that it contacts. This permits the MOP or EOP to draw analytes through semi-permeable membranes and skin for detection by the embedded MRC as described above. Preferably, the MRC-MOP or MRC-EOP may be equipped with a number of molecular recognition sites to perform a complete blood gas, blood electrolyte, hematocrit, blood sugar, and blood metabolite analysis non-invasively (i.e., without drawing blood).

In a preferred embodiment, applied a.c or d.c. electric or magnetic fields are utilized to change the orientational and positional order of liquid crystal biological structures such as cellular membranes, cellular pores, blood vessels, skin, sweat glands, etc. to permit leakage of contained body analytes. A hypertonic junction will pull out, by means of a low chemical potential well, and concentrate leaky analytes. The hypertonic junction is composed of a suitable polyelectrolyte, gel or solid polymer electrolyte (Gray, F M: Solid Polymer Electrolytes. Fundamentals and Technological Applications. VCH Publishers, Inc.; New York, Weinheim, Cambridge; 1991. Hara, M (ed.): Polyelectrolytes. Science and Technology. Marcel Dekker, Inc.; New York, Basel, Hong Kong; 1993) containing an embedded device-based molecular recognition chip (MRC) for detection of specific analyte(s).

VIII. Screening and Assays

A semiconductor surface prepared according to the methods described above can be used, to screen for ligands (i.e., analytes) having high affinity for immobilized molecular recognition sites. A solution containing an unmarked (not labeled) ligand is introduced to the surface. Generally, little or no incubation time is required because of the immediate response of the; molecular recognition chip (MRC) on the order of milliseconds.

Figure 5:
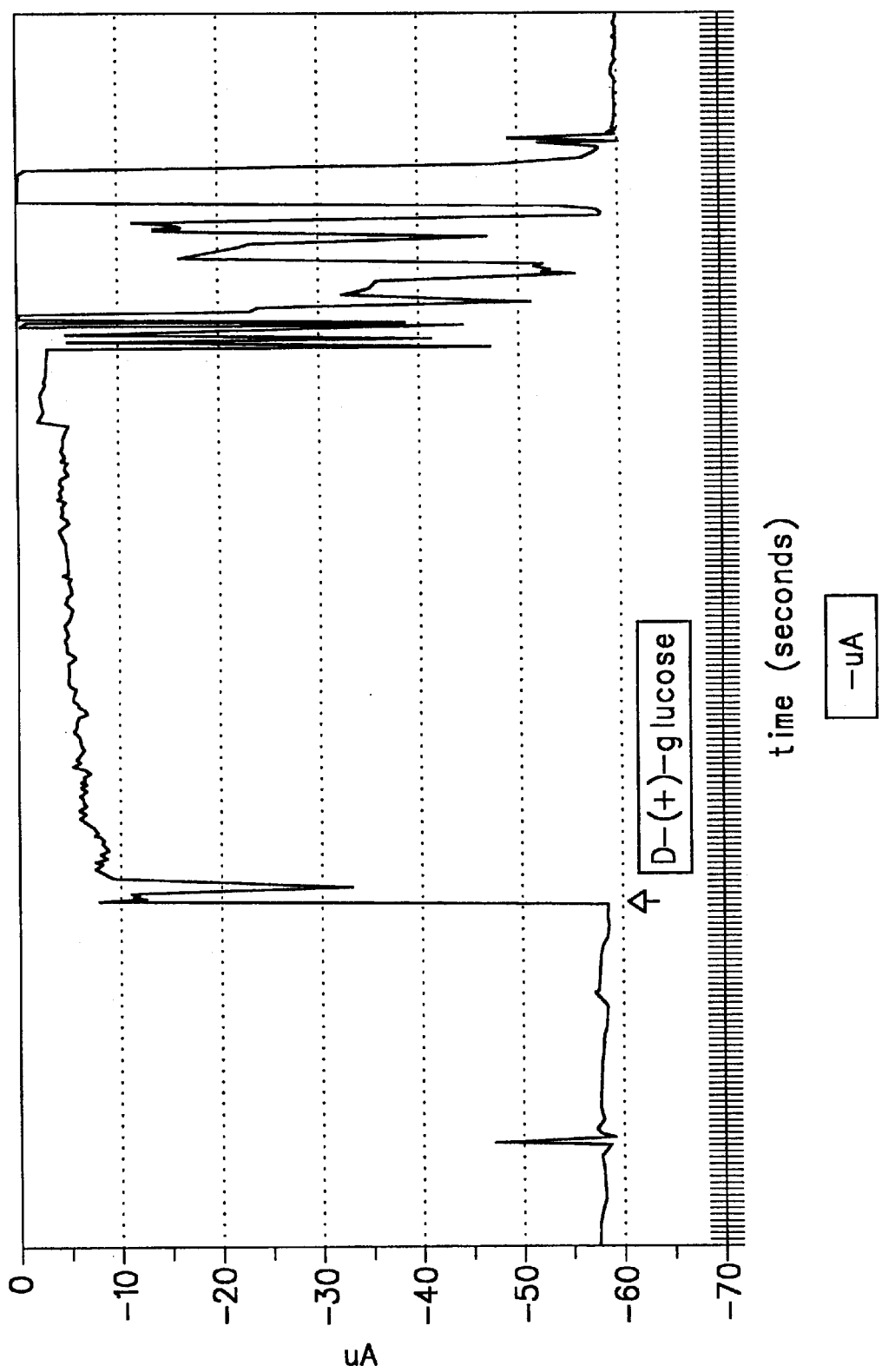
FIG. 5 is a graph showing a current signal generated when glucose is contacted with a photodiode type glucose sensor in accordance with one embodiment of this invention.
Figure 6:
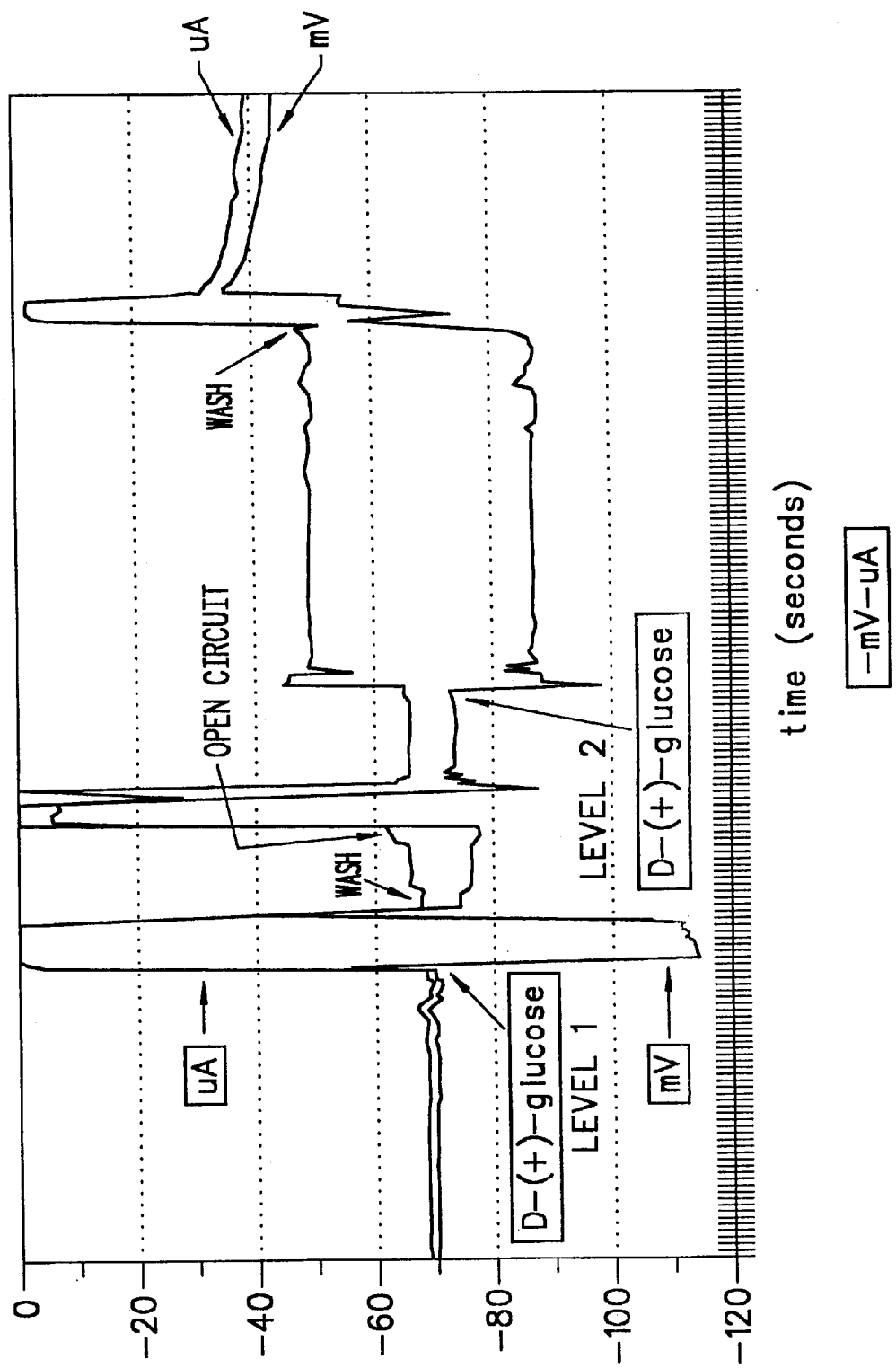
FIG. 6 is a graph showing current voltage signals generated when the sensor employed in FIG. 5 is subjected to a regimen including contact with glucose, washing, open circuit, and recontact with glucose.

In a preferred embodiment, a semiconductor substrate prepared as discussed above is exposed to light while connected to a digital multimeter (MM) which measures the short circuit volt/amp output (i.e., $V_{SC}$, $I_{SC}$) of the p-n junction solar cell substrate (as shown in FIG. 3). The powered chip can now be exposed to a solution containing an unmarked ligand. The unmarked ligand binds with high affinity to an immobilized molecular recognition site previously localized on the chip surface. A square wave signal is generated by the powered chip in less than a few milliseconds in response to the binding event of the ligand (i.e., digital output from the chip). In a preferred embodiment, D-(+)-glucose is applied to the surface of a glucose oxidase-molecular recognition chip (GOD-Chip). The light powered GOD-Chip produces a square wave response in voltlamp output proportional to the applied D-(+)-glucose concentration (see FIGS. 5 and 6 described below). This reflects a change in the short circuit output of the p-n junction solar cell substrate due to electron tunneling from the molecular recognition surface (i.e., GOD) through the highly conductiye polymer monolayer (i.e., liquid-crystal oriented B-DNA) to the p-type surface of the p-n junction solar cell. Carrier injection of electrons by a device into the p-type layer of a powered solar cell substrate interrupts the baseline short circuit photovoltage and photocurrent (i.e., $V_{SC}$, $I_{SC}$) of this simple p-n junction, rectifying diode device. The amount of electrons injected into the p-type surface of the powered chip is proportional to the amount of D-(+)-glucose binding to the GOD, which is reflected in a proportional digital square wave output by the GOD-Chip (FIG. 5 and FIG. 6). Device injection of electrons directly into p-type silicon eliminates or lowers the photocurrent by combination with photogenerated carrier holes, before than can recombine, via short circuit wire, with photogenerated carrier electrons from the n-type layer. Concomitantly with lowered photocurrent resulting from carrier hole removal from the p-type layer, the continued build-up of photogenerated carrier electrons in the n-type layer increases measured photovoltage of the circuit (FIG. 6).

In this embodiment, a simple digital multimeter (voltlamp) is employed to measure the digital output of the GOD-Chip. Therefore, single and multiple IC arrays described above may be configured in pen-based digital meters, hand-held digital meters, clinical lab-based instruments, digital wireless implantable medical devices, and industrial-based digital devices which measure real-time molecular binding events and constants of analytes. A simple calibration curve for each chip can be used to determine the concentration of unknown samples. Calibrated chips are not affected by altitude, humidity, $O_2$ partial pressure, diffusional electron acceptor mediators, or application of the sample. These problems of the prior art, have been overcome in the present invention because electron transfer rates of the molecular wire interconnects are orders of magnitude greater than enzymatic reaction rates, and electron transfer rates of diffusional redox mediators such as $O_2$ and other small molecule inorganic, organometallic, and organic compounds used in amperometric detection methods. A forward electron transfer rate constant ($k_f > 10^7$ s$^{-1}$ Å$^{-2}$) may be very high because of the quantum-wire nature (i.e., defined electronic energy levels) of the conductive polymer interconnects. Connecting polymers may also be reversibly switched between conductive and insulative states by oxidation or reduction.

IX. EXAMPLES

The following examples of prefered embodiments of the present invent;on are presented by way of illustration only and do not suggest that the above-described methods and compositions are in any way limited by the specific examples set forth below.

Example A

Preparation of Polycrystalline Silicon p-n Junction Solar Cell

A commercial polycrystalline silicon p-n junction solar cell chip (a 0.1799 g and 1.75 cm$^2$) from Edmund Scientific, Barrington, N.J. 08007–1380 (Stock Nos. 35,220 and 35,221) was exposed to 980 Lux light intensity from a F15T8/CW Westinghouse bulb at 25° C. With the dark blue emitter surface facing the light source, the short circuit DC output of the dry solar cell substrate was measured by a digital multimeter (DMM) (Extech Instruments; Model No. 383273). Measured DC output was 121 mV and 98 uA. The solar cell chip was then washed with analytical reagent electronic-grade solvents: i) acetone; ii) methanol; iii) 18 Mohm $H_2O$; and iv) methanol. It was allowed to dry in a dust-free environment. This prepared the semiconductor p-n type surfaces for electroplating.

Example B

Electrodeposition of DNA Onto a Polycrystalline Silicon p-n Junction Solar Cell

A DNA electroplating solution was prepared using 18 Mohm sterile water as the solvent. 0.1062 g of DNA (degraded free acid from Herring sperm) was added to 100 ml of water. The pH of the resulting solution was ~2.00. The pH was adjusted to ~7.00 with NaOH and HCl. No buffer was added to the electroplating solution. The final salt/electrolyte concentration was <150 mM. 1.00 mL of methanol was added to the DNA electroplating solution and mixed thoroughly. The dry solar cell chip from Example A produced a short circuit output of 152 mV and 136 uA when exposed to 1700 Lux light intensity generated from two F15T8/CW Westinghouse bulbs at 25° C. The dry solar cell chip from Example A was submerged in the DNA electroplating bath at 25° C. with dark blue emitter surface exposed to 1700 Lux light intensity generated from two F15T8/CW Westinghouse bulbs. After ~5.50 hours, the solar cell chip was removed from the DNA bath and placed on a paper towel to dry. The dark blue emitter surface was exposed to the 1700 Lux light source during the drying process which took ~12.00 hours at 25° C. in air. DNA electroplated on the back or silvery side of the solar cell chip (i.e., p-type silicon) as evidenced by a white coating visible to the eye. On the dark blue emitter surface (i.e., n-type silicon) no significant coating was observed. The pH of the DNA electroplating bath remained ~7.00 after the electroplating process was complete. The electrochemical potential at the plating surface was about 150 mV and the current density wao about 77 $\mu$A cm$^{-2}$.

Example C

Electrodeposition of Glucose Oxidase (GOD) Onto a DNA-Coated Polycrystalline Silicon p-n Junction Solar Cell A glucose oxidase (GOD) electroplating solution was prepared using 18 Mohm sterile water as the solvent. 0.0092 g of glucose oxidase (EC 1.1.3.4; ~1,000 units) was added to 100 ml of water. The pH of the resulting solution was ~6.00. No buffer or further adjustment of pH was necessary. 1.00 ml of methanol was added to the GOD electroplating solution and mixed thoroughly. Next, the DNA-coated polycrystalline silicon p-n junction solar cell from Example B was submerged in the GOD electroplating bath with dark blue emitter surface exposed to 1700 Lux light intensity from two F15T8/CW Westinghouse bulbs at 25° C. for ~8.10 hours. They solar cell chip was removed from the GOD bath and placed on a paper towel to dry. The dark blue emitter surface was exposed to the 1700 Lux light source during the drying process which, took ~12.00 hours at 25° C. in air. GOD electroplated on the back or silvery side of the solar cell chip (i.e., p-type silicon ) as evidenced by a yellow-orange precipitate visible to the eye. The yellow-orange GOD precipitate was in the same area of the chip overlapping the white DNA precipitate from example B. On the dark blue emitter surface (i.e., n-type silicon) no significant coating was observed. T he pH of the GOD electroplating bath remained ~6.00 after the electroplating process was complete. The GOD-DNA-Chip was removed from the light and put under parafilm to protect and store until use. The electrochemical potential at the plating surface was about 150 mV and the current density was about 77 $\mu$A $cm^{-2}$.

EXAMPLE D

Detection of D-(+)-glucose on a GODDNA-Chip.

Coating/electroplating of the solar cell chip from example A did not change the electronic output characteristics of the device prior to testing with the D-(+)-glucose ligand.

The dry GOD-DNA-Chip from example C was placed with the silver GOD-DNA coated surface (i.e., p-type silicon) facing a F15T8/CW Westinghouse bulb. A red (positive) test lead of a digital multimeter (DMM) Extech Instruments; Model No. 383273) was connected to the dark blue emitter (i.e., n-type) surface and the black (negative) test lead was connected to the p-type GOD-DNA coated surface facing the light (FIG. 3). The intensity of light was adjusted to produce a baseline short circuit current of approximately –60 uA (FIG. 5). After several minutes, a drop (~0.0100 to mL) of a sterile D-(+)-glucose standard (63 mg/dL) was placed on the powered GOD-DNA-Chip resulting in a large square wave amplitude change of approximately +51 uA reaching a new baseline of approximately –8 uA (FIG. 5). This is consistent with approximately 2.00× $10^{17}$ glucose molecules being applied to the chip in a 1 $cm^2$ area generating the maximum current expected from a monolayer of well connected GOD. Glucose oxidase (GOD) turns over at ambient temperature at a rate of ~$10^2$ $s^{-1}$, i.e., it produces about 200 transferable electrons/s. Because it has a radius of ~43 Å, there can be up to $1.7\times10^{12}$ enzyme molecules on the electrode surface. The current density, when all redox centers are electrically well connected to the electrode, may thus reach about $3.4\times10^{14}$ electrons $s^{-1}cm^{-2}$, or 53 uA $cm^{-2}$ (Heller, A: Electrical Wiring of Redox Enzymes. Acc. Chem. Res. 23(5):128–134, 1990).

Another test of GOD-DNA-Chip performance at different D-(+)-glucose concentration levels is demonstrated in FIG. 6. "level 1" and "level 2" are sterile D-(+)-glucose standards (~63 and 20 mg/dL respectively). A drop of "level 1" D-(+)-glucose standard produces the first square wave; followed by washing with $H_2O$ and application of the lower "level 2" D-(+)-glucose concentration. Square wave amplitude responses are directly proportional to the D-glucose concentrations applied to the chip. Washing the GOD-DNA-Chip of ligand D-(+)-glucose with $H_2O$ returns the chip to its baseline voltage/current (FIG. 5 and FIG. 6).

CONCLUSION

Various references have been cited in this specification. Each of these references is incorporated herein by reference for all purposes.

The invention has been described primarily with reference to the use of electrochemical deposition of liquid-crystal conductive polymers and molecular recognition surfaces, but it will be readily recognized by those of skill in the art that other types of deposition, conductive wiring, and substrates can be used. Various forms of patterned electrochemical and chemical deposition may be used. Many types of p-n hetero- or homojunction semiconductor substrates may be used. The substrate may be powered by broad spectrum light, light emitting diodes (LED), lasers, solar radiation, uv radiation, vis radiation, infrared radiation, x-rays, gamma rays, radioactivity, thermally, or by any external supplied nuclear or electromagnetic energy greater than the substrate bandgap to provide patterned areas of electrochemical deposition and to power the completed device.

It is understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method of sensing the presence of an analyte component in an analyte with a sensor including (i) a plurality of conductive polymer strands each having at least a first end and a second end and each aligned in a non random orientation, (ii) a plurality of molecular recognition headgroups having an affinity for said analyte component, being attached to said first ends of said conductive polymer strands, and participating in a redox reaction when contacting a molecule of said analyte component, and (iii) an electrode substrate attached to said conductive polymer strands at said second ends, the method comprising:

contacting said molecular recognition headgroups with said analyte; and determining whether mobile charge carriers have been transferred to said electrode substrate resulting from mobile charge carriers generated by said redox reaction and transferred by said conductive polymer strands to said electrode substrate to thereby sense the presence of the analyte component, wherein when said redox reaction occurs at a headgroup, a mobile charge carrier is transferred directly to a conductive polymer strand attached to said headgroup, without redox reaction in the polymer strand.

2. The method of claim 1, further comprising:

monitoring a change in an electronic circuit connected to said electrode substrate, said change resulting from reception of mobile charge carriers from said conductive polymer strands; and correlating said change in said electronic circuit with a concentration of the analyte component.

3. The method of claim 1, wherein the plurality of conductive polymer strands are multi-stranded nucleic acid strands.

4. The method of claim 1, wherein the plurality of conductive polymer strands are double-stranded DNA strands.

5. A method of sensing the presence of an analyte component in an analyte with a sensor including (i) a plurality of molecular recognition headgroups having an affinity for said analyte component, and participating in a redox reaction when contacting a molecule of said analyte component such that when said redox reaction occurs at a headgroup, a mobile charge carrier is generated, and (ii) a diode having a first electrode to which said plurality of molecular recognition headgroups are affixed such that mobile charge carriers generated by said redox reaction are transferred to said first electrode, the method comprising:

contacting said molecular recognition headgroups with said analyte;

specifying a baseline electrical signal that is present when (i) a stimulus is provided to said diode and (ii) said plurality of molecular recognition headgroups are substantially free of said analyte component; and detecting a deviation from said baseline electrical signal to thereby sense the presence of said analyte component, which deviation results from transfer of said mobile charge carriers to the first electrode when the analyte component comes in contact with the molecular recognition headgroups.

6. The method of claim 5, further comprising:

determining an amplitude of said deviation; and determining an analyte component concentration directly from the amplitude of said deviation without the use of any other information from the electrical signal.

7. The method of claim 6, wherein the analyte component concentration is proportional to the amplitude of said deviation.

8. The method of claim 5, wherein the baseline electrical signal and the deviation from the baseline electrical signal are measures of voltage.

9. The method of claim 5, wherein the baseline electrical signal and the deviation from the baseline electrical signal are measures of electrical current.

10. The method of claim 5, wherein the plurality of molecular recognition headgroups are attached to the first electrode via a plurality of conductive polymer strands selected from the group consisting of multi-stranded nucleic acids, electron transport proteins, biopolymers, synthetic organic and inorganic conducting polymers, metal crystallite molecular wires, and Langmuir-Blodgett conducting films.

11. The method of claim 10, wherein the plurality of conductive polymer strands are substantially commonly oriented.

12. The method of claim 5, wherein the diode is a photovoltaic diode and the stimulus provided in the specifying a baseline electrical signal is radiant energy.

13. A method of forming a sensor capable of sensing the presence of an analyte component, the method comprising:

contacting a sensor substrate with a first medium containing mobile conductive polymer'strands or precursors of said conductive polymer strands;

applying a first potential to said substrate sufficient to form a first structure having said conductive polymer strands affixed to said substrate;

contacting said sensor substrate, with affixed conductive polymer strands, with a second medium containing mobile molecular recognition headgroups; and applying a second potential to said substrate sufficient to affix said molecular recognition headgroups to said affixed conductive polymer strands, whereby a sensor structure is formed having said substrate affixed to said conductive polymer strands and said molecular recognition headgroups also affixed to said conductive polymer strands.

14. The method of claim 13, wherein the step of applying a first potential is performed at a potential which causes said affixed conductive polymer strands to be oriented in a non-random direction.

15. The method of claim 14, wherein the first potential is between about 0.001 and 1500 mV.

16. The method of claim 14, wherein the step of applying the first potential produces a current density at the substrate surface of between about 0.001 and 1500 $\mu A\ cm^{-2}$.

17. The method of claim 13, wherein the conductive polymer strands are multi-stranded nucleic acids.

18. The method of claim 13, wherein the step of applying a second potential is performed at a potential which causes said affixed molecular recognition headgroups to be oriented in a non-random direction.

19. The method of claim 18, wherein the second potential is between about 0.001 and 1500 mV.

20. The method of claim 18, wherein the step of applying the first potential produces a current density at the substrate surface of between about 0.001 and 1500 $\mu A\ cm^{-2}$.

21. The method of claim 13, further comprising a step of removing the first medium from the sensor substrate following said step of applying a first potential.

22. The method of claim 13, wherein the second medium is obtained from the first medium by performing the step of applying a first potential.

23. The method of claim 13, wherein the step of applying a first potential to said substrate causes said precursors of said conductive polymer strands to polymerize and form said conductive polymer strands affixed to said substrate.

24. The method of claim 13, wherein the sensor substrate is a device element of a device on semiconductor chip.

25. The method of claim 13, further comprising a step of isolating a region of the sensor substrate prior to the step of contacting said sensor substrate with a second medium, such that the molecular recognition headgroups are deposited only in the isolated region.

26. The method of claim 25, wherein the steps of isolating a region, contacting said sensor substrate with a second medium, and applying a second potential to said substrate are performed a second time, and wherein the step of contacting the sensor substrate with a second medium employs a second medium with a second molecular recognition headgroup, to form a structure having a first region on said sensor substrate having a first group of chemically homogeneous molecular recognition headgroups and a second region on said sensor substrate having a second group of chemically homogeneous molecular recognition headgroups.

27. A sensor produced by the method of claim 13.

* * * * *